US010682397B2

(12) United States Patent
Auerbach et al.

(10) Patent No.: US 10,682,397 B2
(45) Date of Patent: Jun. 16, 2020

(54) METHODS OF TREATING FRAGILE X SYNDROME AND RELATED DISORDERS

(71) Applicants: Massachusetts Institute of Technology, Cambridge, MA (US); Duke University, Durham, NC (US)

(72) Inventors: Benjamin David Auerbach, Buffalo, NY (US); Mark Firman Bear, Boston, MA (US); Laura Jane Stoppel, Cambridge, MA (US); Robert J. Lefkowitz, Durham, NC (US)

(73) Assignees: Massachusetts Institute of Technology, Cambridge, MA (US); Duke University, Durham, NC (US)

( * ) Notice: Subject to any disclaimer, the term of this patent is extended or adjusted under 35 U.S.C. 154(b) by 0 days.

(21) Appl. No.: 15/364,332

(22) Filed: Nov. 30, 2016

(65) Prior Publication Data
US 2017/0157218 A1 Jun. 8, 2017

Related U.S. Application Data

(60) Provisional application No. 62/262,968, filed on Dec. 4, 2015.

(51) Int. Cl.
*C12N 15/11* (2006.01)
*A61K 38/46* (2006.01)
*C12N 15/113* (2010.01)
*C12N 15/115* (2010.01)
*A61K 48/00* (2006.01)

(52) U.S. Cl.
CPC .......... *A61K 38/465* (2013.01); *C12N 15/113* (2013.01); *C12N 15/115* (2013.01); *C12N 15/1138* (2013.01); *A01K 2217/075* (2013.01); *A01K 2217/077* (2013.01); *A01K 2217/15* (2013.01); *A01K 2227/105* (2013.01); *A61K 48/00* (2013.01); *C12N 2310/10* (2013.01); *C12N 2310/11* (2013.01); *C12N 2310/12* (2013.01); *C12N 2310/14* (2013.01); *C12N 2310/16* (2013.01); *C12N 2310/3231* (2013.01); *C12N 2310/3233* (2013.01); *C12N 2310/531* (2013.01)

(58) Field of Classification Search
None
See application file for complete search history.

(56) References Cited

U.S. PATENT DOCUMENTS

2012/0295975 A1* 11/2012 Olefsky .................. A61K 31/20 514/560
2014/0206707 A1 7/2014 Conn et al.
2014/0234972 A1* 8/2014 Zhang .................... C12N 15/63 435/456

OTHER PUBLICATIONS

Osterweil et al, Hypersensitivity to mGluR5 and ERK1/2 Leads to Excessive Protein Synthesis in the Hippocampus of a Mouse Model of Fragile X Syndrome, 2010, The Journal of Neuroscience, 30, 46: 15616-15627.*
Bhakar et al , The Pathophysiology of Fragile X (and What It Teaches Us about Synapses), 2012, Annu. Rev. Neurosci., 35: 417-443.*
DeWire et al, beta-Arrestin-mediated Signaling Regulates Protein Synthesis, 2008, the Journal of Biological Chemistry, vol. 283, 16: 10611-10620.*
Eng et al., mGluR1-β-arrestin 2 signaling mediates induction of excitatory synaptic plasticity. Faseb J. Apr. 2015;29(1). Supplement 935.4.
Eng et al., Transduction of group I mGluR-mediated synaptic plasticity by β-arrestin2 signalling. Nat Commun. Nov. 25, 2016;7:13571. doi: 10.1038/ncomms13571.
Serial No. PCT/US2016/064049, dated Jun. 14, 2018, International Preliminary Report on Patentability.
Abou Farha et al., Metabotropic glutamate receptor 5 negative modulation in phase I clinical trial: potential impact of circadian rhythm on the neuropsychiatric adverse reactions—do hallucinations matter? ISRN Psychiatry. Mar. 14, 2014;2014:652750. doi: 10.1155/2014/652750.
Aguilar-Valles et al., Inhibition of Group I Metabotropic Glutamate Receptors Reverses Autistic-Like Phenotypes Caused by Deficiency of the Translation Repressor eIF4E Binding Protein 2. J Neurosci. Aug. 25, 2015;35(31):11125-32. doi: 10.1523/Jneurosci.4615-14. 2015.
Ahn et al., {beta}-Arrestin-2 Mediates Anti-apoptotic Signaling through Regulation of BAD Phosphorylation. J Biol Chem. Mar. 27, 2009;284(13):8855-65. doi: 10.1074/jbc.M808463200.
Auerbach et al., Mutations causing syndromic autism define an axis of synaptic pathophysiology. Nature. Nov. 23, 2011;480(7375):63-8. doi: 10.1038/nature10658.
Banko et al., Regulation of eukaryotic initiation factor 4E by converging signaling pathways during metabotropic glutamate receptor-dependent long-term depression. J Neurosci. Feb. 22, 2006;26(8):2167-73.
Barnes et al., Convergence of Hippocampal Pathophysiology in Syngap+/− and Fmr1−/y Mice. J Neurosci. Nov. 11, 2015;35(45):15073-81. doi: 10.1523/Jneurosci.1087-15.2015.
Bhakar et al., The pathophysiology of fragile X (and what it teaches us about synapses). Annu Rev Neurosci. 2012;35:417-43. doi: 10.1146/annurev-neuro-060909-153138.
Bozdagi et al., Haploinsufficiency of the autism-associated Shank3 gene leads to deficits in synaptic function, social interaction, and social communication. Mol Autism. Dec. 17, 2010;1(1):15. doi: 10.1186/2040-2392-1-15.
Dewire et al., Beta-arrestin-mediated signaling regulates protein synthesis. J. Biol. Chem. Feb. 14, 2008; 283(16):10611-20.
Dolen et al., Correction of fragile X syndrome in mice. Neuron. Dec. 20, 2007;56(6):955-62.
Fan et al., Rapid and reversible knockdown of endogenous proteins by peptide-directed lysosomal degradation. Nat Neurosci. Mar. 2014;17(3):471-80. doi: 10.1038/nn.3637.

(Continued)

*Primary Examiner* — Ekaterina Poliakova-Georgantas
(74) *Attorney, Agent, or Firm* — Wolf, Greenfield & Sacks, P.C.

(57) ABSTRACT

Disclosed herein are novel methodologies of treating fragile X syndrome and related disorders by inhibiting mGlu$_5$-relevant signaling pathways via the reduction of β-arrestin2 protein levels or the diminution of mGlu$_5$ and β-arrestin2 protein interactions.

9 Claims, 8 Drawing Sheets

Specification includes a Sequence Listing.

(56) References Cited

OTHER PUBLICATIONS

Gallagher et al., Extracellular signal-regulated protein kinase activation is required for metabotropic glutamate receptor-dependent long-term depression in hippocampal area CA1. J Neurosci. May 19, 2004;24(20):4859-64.
Hathaway et al., Pharmacological characterization of mGlu1 receptors in cerebellar granule cells reveals biased agonism. Neuropharmacology. Jun. 2015;93:199-208. doi: 10.1016/j.neuropharm.2015.02.007.
Homayoun et al., Functional Interaction Between NMDA and mGlu5 Receptors: Effects on Working Memory, Instrumental Learning, Motor Behaviors, and Dopamine Release. Neuropsychopharmacology. Jul. 2004;29(7):1259-69.
Huber et al., Chemical induction of mGluR5- and protein synthesis-dependent long-term depression in hippocampal area CA1. J Neurophysiol. Jul. 2001;86(1):321-5.
Insel et al., Impact of GPCRs in clinical medicine: monogenic diseases, genetic variants and drug targets. Biochim Biophys Acta. Apr. 2007;1768(4):994-1005.
Kotula et al., Targeted disruption of β-arrestin 2-mediated signaling pathways by aptamer chimeras leads to inhibition of leukemic cell growth. PLoS One. Apr. 15, 2014;9(4):e93441. doi: 10.1371/journal.pone.0093441.
Marschall et al., Antibodies inside of a cell can change its outside: Can intrabodies provide a new therapeutic paradigm? Comput Struct Biotechnol J. Jul. 31, 2016;14:304-8. doi: 10.1016/j.csbj.2016.07.003.
Osterweil et al., Hypersensitivity to mGluR5 and ERK1/2 leads to excessive protein synthesis in the hippocampus of a mouse model of fragile X syndrome. J. Neurosci. Nov. 17, 2010;30(46):15616-27.
Osterweil et al., Lovastatin corrects excess protein synthesis and prevents epileptogenesis in a mouse model of fragile X syndrome. Neuron. Jan. 23, 2013;77(2):243-50. doi: 10.1016/j.neuron.2012.01.034.
Qin et al., Increased rates of cerebral glucose metabolism in a mouse model of fragile X mental retardation. Proc Natl Acad Sci U S A. Nov. 26, 2002;99(24):15758-63.
Richter et al., Dysregulation and restoration of translational homeostasis in fragile X syndrome. Nat Rev Neurosci. Oct. 2015;16(10):595-605. doi: 10.1038/nrn4001.
Sheffler et al., Allosteric modulation of metabotropic glutamate receptors. Adv Pharmacol. 2011;62:37-77. doi: 10.1016/B978-0-12-385952-5.00010-5.
Tian et al., Contribution of mGluR5 to pathophysiology in a mouse model of human chromosome 16p11.2 microdeletion. Nat Neurosci. Feb. 2015;18(2):182-4. doi: 10.1038/nn.3911.
Wenger et al., The Role of mGluR Copy Number Variation in Genetic and Environmental Forms of Syndromic Autism Spectrum Disorder. Sci Rep. Jan. 19, 2016;6:19372. doi: 10.1038/srep19372.
Whalen et al ., Therapeutic potential of β-arrestin- and G protein-biased agonists. Trends Mol Med. Mar. 2011;17(3):126-39. doi: 10.1016/j.molmed.2010.11.004.
Berry-Kravis et al., Mavoglurant in fragile X syndrome: Results of two randomized, double-blind, placebo-controlled trials. Sci Transl Med. Jan. 13, 2016;8(321):321ra5. doi: 10.1126/scitranslmed.aab4109.
Cosford et al., 3-[(2-Methyl-1,3-thiazol-4-yl)ethynyl]-pyridine: a potent and highly selective metabotropic glutamate subtype 5 receptor antagonist with anxiolytic activity. J Med Chem. Jan. 16, 2003;46(2):204-6.
Dewire et al., Beta-arrestins and cell signaling. Annu Rev Physiol. 2007;69:483-510.
Gasparini et al., 2-Methyl-6-(phenylethynyl)-pyridine (MPEP), a potent, selective and systemically active mGlu5 receptor antagonist. Neuropharmacology. Oct. 1999;38(10):1493-503.
Huber et al., Role for rapid dendritic protein synthesis in hippocampal mGluR-dependent longterm depression. Science. May 19, 2000;288(5469):1254-7.
Iacovelli et al., Selective regulation of recombinantly expressed mGlu7 metabotropic glutamate receptors by G protein-coupled receptor kinases and arrestins. Neuropharmacology. Feb. 2014;77:303-12. doi: 10.1016/j.neuropharm.2013.10.013.
Lindemann et al., CTEP: a novel, potent, long-acting, and orally bioavailable metabotropic glutamate receptor 5 inhibitor. J Pharmacol Exp Ther. Nov. 2011;339(2):474-86. doi: 10.1124/jpet.111.185660.
Pecknold et al., Treatment of anxiety using fenobam (a nonbenzodiazepine) in a double-blind standard (diazepam) placebo-controlled study. J Clin Psychopharmacol. Apr. 1982;2(2):129-33.
Pietraszek et al., mGluR5, but not mGluR1, antagonist modifies MK-801-induced locomotor activity and deficit of prepulse inhibition. Neuropharmacology. Jul. 2005;49(1):73-85.
Pop et al., Fragile X syndrome: a preclinical review on metabotropic glutamate receptor 5 (mGluR5) antagonists and drug development. Psychopharmacology (Berl). Mar. 2014;231(6):1217-26.
Porter et al., Fenobam: a clinically validated nonbenzodiazepine anxiolytic is a potent, selective, and noncompetitive mGlu5 receptor antagonist with inverse agonist activity. J Pharmacol Exp Ther. Nov. 2005;315(2):711-21.
Scharf et al., Metabotropic glutamate receptor 5 as drug target for Fragile X syndrome. Curr Opin Pharmacol. Feb. 2015;20:124-34. doi: 10.1016/j.coph.2014.11.004.
Schnabel et al., An investigation into signal transduction mechanisms involved in DHPG-induced LTD in the CA1 region of the hippocampus. Neuropharmacology. Oct. 1999;38(10):1585-96.
Yan et al., Suppression of two major Fragile X Syndrome mouse model phenotypes by the mGluR5 antagonist MPEP. Neuropharmacology. Dec. 2005;49(7):1053-66.

* cited by examiner

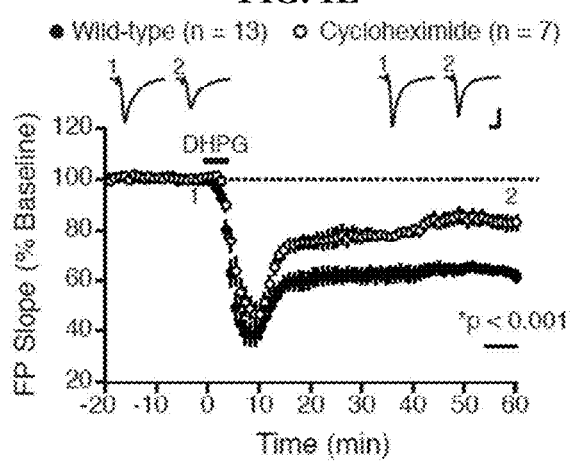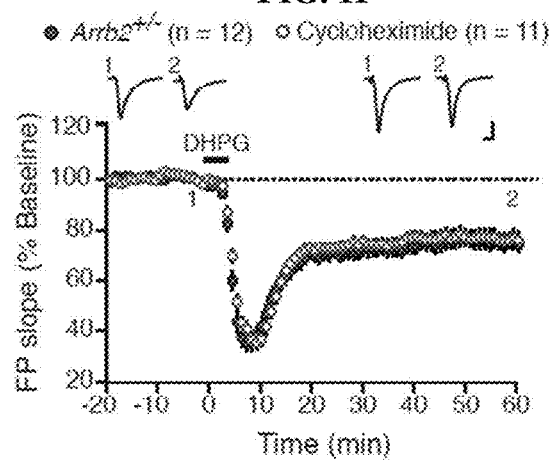

FIG. 3C
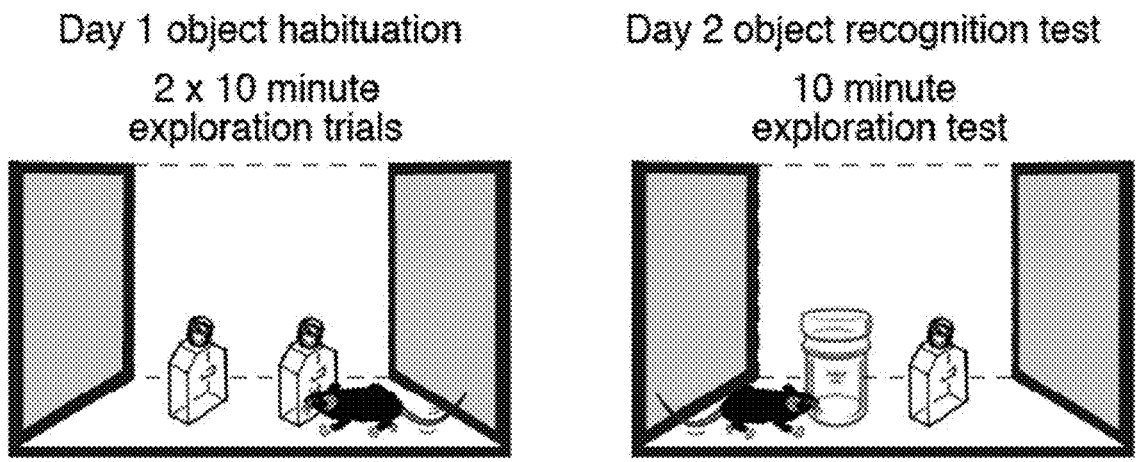
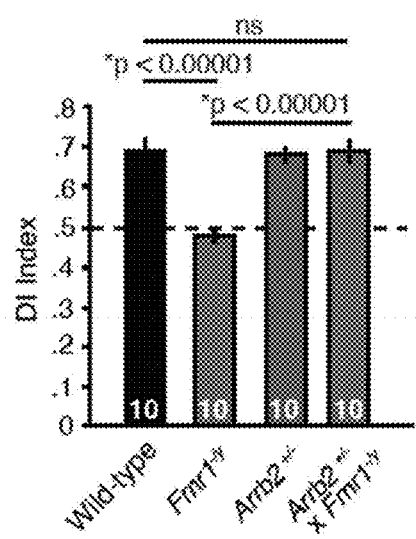
FIG. 3D
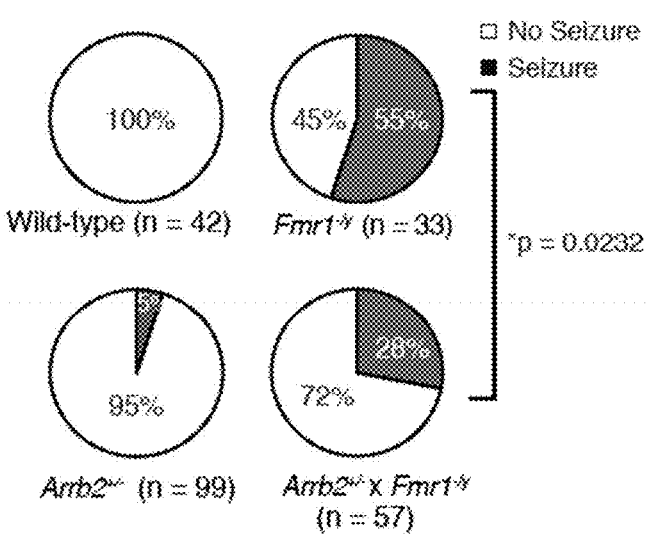
FIG. 3E

METHODS OF TREATING FRAGILE X SYNDROME AND RELATED DISORDERS

RELATED APPLICATION

This application claims the benefit under 35 U.S.C. § 119(e) of U.S. Provisional Application Ser. No. 62/262,968, filed on Dec. 4, 2015, the entire content of which is herein incorporated by reference.

GOVERNMENT SUPPORT

This invention was made with Government support under Grant No. R21 NS087225 awarded by the National Institutes of Health, and under Grant No. W81XWH-11-1-0252 awarded by the U.S. Army Medical Research and Material Command The Government has certain rights in the invention.

FIELD

Disclosed herein are novel methodologies of treating fragile X syndrome and related disorders by inhibiting mGlu$_5$-relevant signaling pathways via the reduction of β-arrestin2 protein levels or the diminution of mGlu$_5$ and β-arrestin2 protein interactions.

BACKGROUND

Numerous genetic and molecular studies have demonstrated that poorly regulated synaptic protein synthesis downstream of metabotropic glutamate receptor 5 (mGlu$_5$) contributes to the pathophysiology of fragile X (FX), a genetic cause of intellectual disability (ID) and autism spectrum disorder (ASD) (Pop et al., 2014). These studies suggest that targeting mGlu$_5$ or its downstream effectors may be a fruitful approach for improving the course of FX and other genetic syndromes with shared pathophysiology (Aguilar-Valles et al., J. Neurosci. 31, 11125-32 (2015); Auerbach et al., Nature 7375, 63-8 (2011); Barnes et al., J. Neurosci. 45, 15073-81 (2015); Bozdagi et al., Mol. Autism 1, 15 (2010); Tian et al., Nat. Neurosci. 2, 182-84 (2015); Wenger et al., Sci. Rep. 6, 19372 (2016)). Indeed, mGlu$_5$-based therapies have been immensely successful at correcting FX in animal models (Bhakar et al., Ann. Rev. Neurosci. 45, 417-43 (2012)). To date, however, the results of human clinical trials in FX using mGlu$_5$ negative allosteric modulators (NAMs) have been disappointing (Berry-Kravis et al., Sci. Transl. Med. 321, 321ra5 (2016); Scharf et al., Curr. Opin. Pharmacol. 20, 124-34 (2015)).

SUMMARY

Fragile X, a heritable cause of autism and intellectual disability, is characterized by aberrant synaptic protein synthesis, which is essential for modification of the brain by experience. Neural activity directs local protein synthesis via activation of metabotropic glutamate receptor 5 (mGlu$_5$), yet how mGlu$_5$ couples to the intracellular signaling pathways that regulate mRNA translation is poorly understood. While some mGlu$_5$-based therapies have demonstrated potential in FX animal models (Bhakar et al., Ann. Rev. Neurosci. 45, 417-43 (2012)), human clinical trials in FX using mGlu$_5$ negative allosteric modulators have been disappointing (Berry-Kravis et al., Sci. Transl. Med. 321, 321ra5 (2016); Scharf et al., Curr. Opin. Pharmacol. 20, 124-34 (2015)). Alternate approaches that overcome the limitations of current methodologies of inhibiting mGlu$_5$ activity are, therefore, desirable.

mGlu$_5$-based therapies also have potential for the treatment of fragile X-related disorders including fragile X-associated primary ovarian insufficiency, fragile X-associated tremor/ataxia syndrome, an autism spectrum disorder, or tuberous sclerosis (Aguilar-Valles et al., J. Neurosci. 31, 11125-32 (2015); Auerbach et al., Nature 7375, 63-8 (2011); Barnes et al., J. Neurosci. 45, 15073-81 (2015); Bozdagi et al., Mol. Autism 1, 15 (2010); Tian et al., Nat. Neurosci. 2, 182-84 (2015); Wenger et al., Sci. Rep. 6, 19372 (2016)).

Described herein are novel methods of treating fragile X syndrome and related disorders. These methods relate to the discovery, disclosed herein, that β-arrestin2 couples mGlu$_5$ to synaptic protein synthesis. In some embodiments a subject suffering from fragile X syndrome is administered an effective amount of a therapeutic compound that reduces β-arrestin2 protein levels. In other embodiments, the subject is administered an effective amount of a compound that inhibits or otherwise negatively modulates the interaction between mGlu$_5$ and β-arrestin2 proteins in said subject. In some embodiments, the subject is suffering from fragile X-associated primary ovarian insufficiency, fragile X-associated tremor/ataxia syndrome, an autism spectrum disorder, or tuberous sclerosis. In some embodiments, the reduction of β-arrestin2 protein levels or inhibition of the interaction between mGlu$_5$ and β-arrestin2 proteins ameliorates exaggerated protein synthesis, altered synaptic plasticity, or behavioral impairments in fragile X syndrome or a related disorder.

Inhibition of β-arrestin2 protein levels can be achieved at the level of DNA, RNA or protein. At the level of DNA, genome editing techniques can knockout or disrupt the β-arrestin2 gene (i.e., ARRB2) or prevent the initiation of β-arrestin2 gene transcription. Perturbations of β-arrestin2 mRNA through disruption of gene splicing, mRNA translation, or mRNA stability can also result in decreased protein levels. Finally, at the protein level, β-arrestin2 levels can be modulated via inhibiting its transport to the area of interest (i.e., the synapse) or by targeting the protein for degradation.

In some embodiments, the therapeutic compound includes a gene therapy that knocks out or disrupts the β-arrestin2 gene. Relevant genome editing techniques include, but are not limited to: zinc finger nucleases, transcription activator-like effector nucleases (TALENs), meganucleases, and CRISPR/Cas9 nuclease systems.

In some embodiments, the therapeutic compound includes an inhibitory molecule that alters β-arrestin2 mRNA splicing, stability, or translation. In some embodiments, the inhibitory molecule is a nucleic acid. In some embodiments, the inhibitory nucleic acid molecule is an antisense nucleic acid, a locked nucleic acid molecule, a peptide nucleic acid molecule, a morpholino, a siRNA molecule, a shRNA molecule or a ribozyme.

In some embodiments, local β-arrestin2 protein levels are modulated via inhibiting the transport of β-arrestin2 to the area of interest (i.e., the synapse). In other embodiments, β-arrestin2 protein levels are modulated via targeting the protein for degradation.

In some embodiments, the therapeutic compound includes a molecule that inhibits or otherwise negatively modulates the interaction between mGlu$_5$ and β-arrestin2 proteins. In some embodiments, the therapeutic compound includes a molecule that binds to a β-arrestin2 protein. In other embodiments, the compound includes a molecule that binds to a mGlu$_5$ protein. In the context of disrupting the interaction between proteins, relevant molecules include, but are not limited to an antibody, an intrabody, an aptamer, or a small molecule.

In some embodiments, the therapeutic compound contains a cocktail of at least two molecules that inhibit β-arrestin2 protein levels and/or inhibit the interaction between mGlu$_5$ and β-arrestin2 proteins.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1F. β-arrestin2 is necessary for protein synthesis-dependent mGlu-LTD and ERK1/2 activation. FIG. 1A. Schematic illustrates experimental timeline. Protein synthesis was elevated in WT slices stimulated with CDPPB compared with vehicle whereas treatment had no effect in Arrb2$^{+/-}$ slices (two-way ANOVA, genotype vs. treatment, *p=0.012). FIG. 1B. Representative immunoblots of ERK1/2 phosphorylation and total ERK protein from hippocampal slices±CDPPB stimulation from WT and Arrb2$^{+/-}$ mice. WT slices stimulated with CDPPB show elevated ERK1/2 phosphorylation compared with vehicle, whereas no change is observed in Arrb2$^{+/-}$ mice (two-way ANOVA, genotype vs. treatment, *p=0.015). FIG. 1C. Quantification of calcium fluorescence over time in WT and Arrb2$^{+/-}$ slices. Data are normalized as ΔF/F. There is no significant difference in the peak calcium fluorescence measured between WT and Arrb2$^{+/-}$ slices (Mann-Whitney test, p=0.7959). FIG. 1D. The cumulative probability of peak fluorescence for all cells analyzed is not different between WT and Arrb2$^{+/-}$ slices (Kolmogorov-Smirnov test, p=0.8334). FIG. 1E. DHPG-LTD (25 μM, 5 min) is significantly attenuated by pretreatment with the protein synthesis inhibitor cycloheximide (CHX, 60 μM) in slices from WT animals (*p<0.001). FIG. 1F. CHX treatment has no effect on DHPG-LTD in slices from Arrb2$^{+/-}$ mice. Representative field potential (FP) traces (average of 10 sweeps) were taken at times indicated by numerals. Scales bars equal 0.5 mV, 5 ms. For this and all subsequent figures data is plotted as mean±s.e.m. Statistics were performed using each animal as one "n," with each animal represented by the mean of 1-4 slices, unless otherwise noted. All experiments were performed blind to genotype and include interleaved controls for genotype and treatment.

FIG. 2A. Genetic rescue strategy. FIG. 2B. Basal protein synthesis is significantly increased in slices from Fmr1$^{-/y}$ mice (*p<0.0001) compared with WT slices. Basal protein synthesis is comparable in slices from Arrb2$^{+/-}$×Fmr1$^{-/y}$ mice and WT mice. FIG. 2C. The magnitude of DHPG-induced LTD in slices from Arrb2$^{+/-}$×Fmr1$^{-/y}$ mice is significantly different from Fmr1$^{-/y}$ slices (*p<0.03), and is indistinguishable from WT slices. Representative field potential traces (average of 10 sweeps) were taken at times indicated by numerals. Scales bars equal 0.5 mV, 2 ms. FIG. 2D. Summary of LTD data. Bar graphs, percentage decrease from baseline in fEPSP slope.

FIGS. 3A-3E. Genetic reduction of β-arrestin2 in Fmr1$^{-/y}$ mice corrects behavioral and cognitive deficits. FIG. 3A. Experimental design of inhibitory avoidance learning task. FIG. 3B. Fmr1$^{-/y}$ mice and Arrb2$^{+/-}$ mice show impaired acquisition of inhibitory avoidance learning compared to WT mice (two-way ANOVA, *p<0.001 for each comparison, wild-type vs. Fmr1$^{-/y}$, WT vs. Arrb2$^{+/-}$). Arrb2$^{+/-}$× Fmr1$^{-/y}$ mice show comparable acquisition and extinction of inhibitory avoidance to WT mice (two-way ANOVA, p=0.916). There is a statistically significant interaction between genotype and time point across groups (repeated measures two-way ANOVA, *p=<0.001). FIG. 3C. Experimental design of familiar object recognition task. FIG. 3D. Fmr1$^{-/y}$ mice show impaired novelty detection on experimental test day 2 when presented with a familiar and novel object compared to WT (*p<0.00001). In comparison, Arrb2$^{+/-}$×Fmr1$^{-/y}$ show a discrimination index that is not significantly different from wild-type mice (Student's two-tailed t-test, p=0.9598). FIG. 3E. Fmr1$^{-/y}$ mice exhibit increased susceptibility to audiogenic seizure activity compared to WT (two-tailed Fisher's exact test, *p=0.0001) and Arrb2$^{+/-}$ mice (*p=0.0001). Genetic reduction of Arrb2 in Fmr1$^{-/y}$ mice significantly reduces the incidence of seizure activity (*p=0.0232).

FIG. 5A. Schematic illustrates experimental timeline. Protein synthesis was similarly elevated in WT slices and Arrb1$^{+/-}$ slices stimulated with CDPPB compared to vehicle-treated slices of both genotypes (two-way ANOVA, genotype vs. treatment, p=0.589). FIG. 5B. Schematic illustrates experimental timeline. Representative immunoblots of ERK1/2 phosphorylation and total ERK protein from hippocampal slices±10 μM CDPPB stimulation from WT and Arrb1$^{+/-}$ mice. WT and Arrb1$^{+/-}$ slices stimulated with CDPPB show elevated ERK1/2 phosphorylation compared with vehicle, (two-way ANOVA, genotype vs. treatment, p=0.786).

FIG. 6A. Representative immunoblots of AKT phosphorylation and total AKT protein from hippocampal slices±10 μM CDPPB stimulation from WT and Arrb1$^{+/-}$ mice. Neither WT nor Arrb1$^{+/-}$ slices stimulated with CDPPB show elevated AKT phosphorylation compared with vehicle, (two-way ANOVA, genotype vs. treatment, p=0.727). FIG. 6B. Representative immunoblots of ribosomal protein S6 phosphorylation and total S6 protein from hippocampal slices±10 μM CDPPB stimulation from WT and Arrb1$^{+/-}$ mice. Neither WT nor Arrb1$^{+/-}$ slices stimulated with CDPPB show elevated S6 phosphorylation compared with vehicle, (two-way ANOVA, genotype vs. treatment, p=0.945). FIG. 6C. Representative immunoblots of AKT phosphorylation and total AKT protein from hippocampal slices±10 μM CDPPB stimulation from WT and Arrb2$^{+/-}$ mice. Neither WT nor Arrb2$^{+/-}$ slices stimulated with CDPPB show elevated AKT phosphorylation compared with vehicle, (two-way ANOVA, genotype vs. treatment, p=0.894). FIG. 6D. Representative immunoblots of ribosomal protein S6 phosphorylation and total S6 protein from hippocampal slices±10 μM CDPPB stimulation from WT and Arrb2$^{+/-}$ mice. Neither WT nor Arrb2$^{+/-}$ slices stimulated with CDPPB show elevated S6 phosphorylation compared with vehicle, (two-way ANOVA, genotype vs. treatment, p=0.920).

FIG. 7A. Basal synaptic transmission (plotted as fEPSP amplitude against presynaptic fiber volley amplitude) does not differ between genotypes. Scale bars equal 0.5 mV, 20 ms for representative field potential traces. FIG. 7B. Paired pulse facilitation is normal across several inter-stimulus intervals (20, 30, 50, 100, 200, 300, 500 ms) in Arrb2$^{+/-}$ slices. Scale bars equal 0.5 mV, 20 ms. FIG. 7C. There is no significant difference in paired pulse facilitation between WT and Arrb2$^{+/-}$ mice with or without the presence of cycloheximide FIG. 7D. The magnitude of NMDA receptor-dependent LTD evoked by low frequency stimulation (LFS, 900 pulses at 1 Hz) does not differ between genotypes (p=0.610). Representative field potential traces (average of 10 sweeps) were taken at times indicated by numerals. Scales bars equal 0.5 mV, 5 ms.

DETAILED DESCRIPTION

Figure 1A:
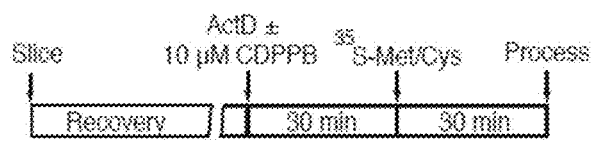
Figure 1A:
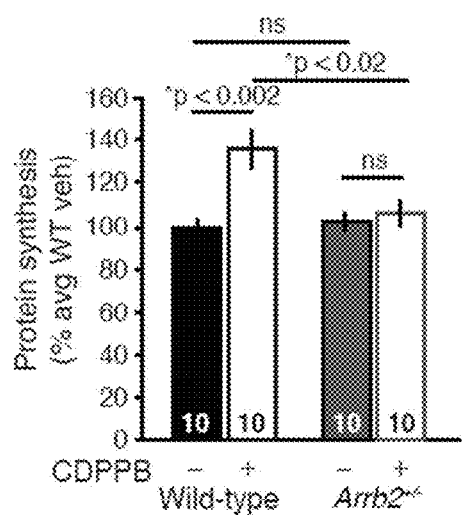

Fragile X, a heritable cause of autism and intellectual disability, is characterized by aberrant synaptic protein synthesis. It has been known for several decades that excitatory synapses in the brain have the machinery necessary to direct synthesis of new protein and that one major regulator of this local protein synthesis is mGlu$_5$. While some mGlu$_5$-based therapies have demonstrated potential in FX animal models (Bhakar et al., Ann. Rev. Neurosci. 45, 417-43 (2012)), human clinical trials in FX using mGlu$_5$ negative allosteric modulators (NAMs) have been disappointing (Berry-Kravis et al., Sci. Transl. Med. 321, 321ra5 (2016); Scharf et al., Curr. Opin. Pharmacol. 20, 124-34 (2015)). Although many factors contribute to the challenge of translating findings from animal models to humans, one factor that is common to all drug trials is the therapeutic window the range of doses that can treat disease pathophysiology without causing negative side effects. In humans, for example, it has been reported that inhibition of mGlu$_5$ produces dose-limiting psychotomimetic effects (Abou Farha et al., ISRN Psychiatry, 652750 (2014); Pecknold et al., J. Clin. Psychopharmacology 2, 129-33 (1982); Porter et al., J. Pharmacol. Exp. Ther. 2, 711-21 (2005)). The first-generation mGlu$_5$ NAMs were identified based on their ability to inhibit G$_q$ signaling mediated by phosphoinositide hydrolysis and release of Ca$^{2+}$ from intracellular stores (Cosford et al., J. Med. Chem. 2, 204-5 (2003); Gasparini et al., Neuropharmacology, 10, 1493-503 (1999); Lindemann et al., J. Pharmacol. Exp. Ther. 2, 474-86 (2011)). However, available data suggest alternative signaling pathways are central to the regulation of synaptic protein synthesis by mGlu$_5$ (Bhakar et al., Ann. Rev. Neurosci. 45, 417-43 (2012); Osterweil et al., Neuron, 243-50 (2013); Richter et al., Nat. Rev. Neurosci. 10, 595-605 (2015)). Ideally, therapeutic effects can be enhanced and separated from side effects by selectively targeting the coupling of mGlu$_5$ to disease-relevant signaling pathway(s).

To separate the therapeutic effect of mGlu$_5$ inhibition (suppression of protein synthesis) from the unwanted side effects, it is essential to understand the mechanism that specifically couples mGlu$_5$ to the ERK signaling pathway. G-protein coupled receptors respond to a wide variety of signals and initiate a large number of distinct cellular signaling pathways. This versatility has made these receptors attractive targets for pharmacological therapies, and over 50% of the current drugs used clinically target these receptors (Insel et al., Biochim. Biophys. Acta. 4, 994-1005 (2007)). However, a number of lines of evidence have previously suggested that "canonical" G-protein signaling is not involved directly in the control of synaptic protein synthesis by mGlu$_5$ (Gallagher et al., J. Neurosci. 20, 4859-64 (2004); Osterweil et al., J. Neurosci. 46, 15616-27 (2010); Schnabel et al., Neuropharmacology 10, 1585-96 (1999)). Instead, the data indicate that mGlu$_5$-stimulated protein synthesis occurs downstream of independently regulated pathways, including one mediated by ERK.

One pathway that is known to be central to mGlu$_5$-stimulated protein synthesis and FX pathophysiology culminates in activation of ERK1/2 and the phosphorylation of proteins involved in the regulation of cap-dependent mRNA translation (Banko et al., J. Neurosci. 8, 2167-73 (2006); Osterweil et al., Neuron, 243-50 (2013); Osterweil et al., J. Neurosci. 46, 15616-27 (2010)). Activation of this pathway by mGlu$_5$ can occur independently of G-protein signaling, but how this is achieved has remained a mystery.

As is the case for many seven-transmembrane domain receptors, G-protein signaling of ligand-bound mGlu$_5$ is terminated by recruitment of β-arrestin to the carboxyl tail of the receptor. In recent years it has become clear that β-arrestin recruitment can also trigger activation of alternative signaling cascades. Of particular relevance is the observation that β-arrestin2 recruitment to the angiotensin II receptor (which, like mGlu$_5$, is also G$_q$-coupled) stimulates the ERK1/2 pathway and increases mRNA translation rates in both human embryonic kidney 293 and rat vascular smooth muscle cells (Ahn et al., 2009; DeWire et al., J. Biol. Chem. 16, 10611-20 (2008)).

Described herein are novel methods of treating fragile X syndrome and related disorders. These methods relate to the discovery, disclosed herein, that β-arrestin2 mediates mGlu$_5$-stimulated protein synthesis in the hippocampus and that genetic reduction of β-arrestin2 corrects aberrant synaptic plasticity and cognition in the Fmr1$^{-/y}$ mouse model of fragile X. Importantly, reducing β-arrestin2 does not induce psychotomimetic activity associated with full mGlu$_5$ inhibitors, and does not affect G$_q$ signaling. Thus, β-arrestin2-biased negative modulators offer significant advantages over first-generation Mglu$_5$ inhibitors for the treatment of fragile X and related disorders.

As used herein "treating" can include: improving one or more symptoms of a disorder; curing a disorder; preventing a disorder from becoming worse; slowing the rate of progression of a disorder; or preventing a disorder from re-occurring.

In some embodiments of the disclosed invention, the subject is suffering from fragile X syndrome. In some embodiments, the subject is suffering from fragile X-associated primary ovarian insufficiency, fragile X-associated tremor/ataxia syndrome, an autism spectrum disorder, or tuberous sclerosis. In some embodiments, the subject is a subject having, suspected of having, or at risk of developing fragile X syndrome, fragile X-associated primary ovarian insufficiency, fragile X-associated tremor/ataxia syndrome, an autism spectrum disorder, or tuberous sclerosis. In some embodiments, the subject is a mammalian subject, including but not limited to a dog, cat, horse, cow, pig, sheep, goat, rodent, or primate. In some embodiments, the subject is a human subject, such as a human patient. In some embodiments, the subject is a human embryo or fetus. The terms "patient," "subject," or "individual" may be used interchangeably and refer to a subject who is in need of the treatment as described herein. Such a subject may exhibit one or more symptoms associated with the disorder. Alternatively or in addition, such a subject may carry or exhibit one or more risk factors for the disorder. In some embodiments, the subject has been diagnosed with fragile X syndrome, fragile X-associated primary ovarian insufficiency, fragile X-associated tremor/ataxia syndrome, an autism spectrum disorder, or tuberous sclerosis.

In some embodiments of the disclosed invention, a subject suffering from fragile X syndrome is administered an effective amount of a therapeutic compound that reduces β-arrestin2 protein levels. In other embodiments, the subject is administered an effective amount of a compound that inhibits the interaction between mGlu$_5$ and β-arrestin2 proteins in said subject. In some embodiments, the reduction of β-arrestin2 protein levels or inhibition of the interaction between mGlu$_5$ and β-arrestin2 proteins ameliorates exaggerated protein synthesis, altered synaptic plasticity, or behavioral impairments in the fragile X syndrome or related disorder.

Inhibition of β-arrestin2 protein levels can be achieved at the level of DNA, RNA or protein. At the level of DNA, genome editing techniques can knockout or disrupt the β-arrestin2 gene (i.e., ARRB2) or prevent the initiation of β-arrestin2 gene transcription. Perturbations of β-arrestin2 mRNA through disruption of gene splicing, mRNA translation, or mRNA stability can also result in decreased protein levels. Finally, at the protein level, β-arrestin2 levels can be modulated via inhibiting its transport to the area of interest (i.e., the synapse) or by targeting the protein for degradation.

In some embodiments, the therapeutic compound includes a gene therapy that knocks out or disrupts the β-arrestin2 gene. Relevant genome editing techniques include, but are not limited to: zinc finger nucleases, transcription activator-like effector nucleases (TALENs), meganucleases, and CRISPR/Cas9 nuclease systems. As used herein, a "knockout" includes mutations such as, a point mutation, an insertion, a deletion, a frameshift, or a missense mutation. Knockouts may be limited to the tissue where β-arrestin2 expression is problematic (e.g., neuronal cells). Additional temporal controls may be introduced via gene editing. These temporal controls include, but are not limited to, driving the expression of molecules (e.g., nucleases) that disrupt the β-arrestin2 gene at certain stages of development or growth.

As used herein, an "effective amount" of a gene therapy is an amount sufficient to impede the levels of the target mRNA or protein, an amount sufficient to decrease synaptic protein synthesis, or an amount sufficient to ameliorate a subject's symptoms arising due to fragile X or a related disorder. Decreases in target mRNA or protein levels and in synaptic protein synthesis can be detected using standard techniques known in the art. One skilled in the art can readily determine an effective amount of the gene therapy to be administered to a given subject. In some embodiments, treatment with a gene therapy will result in a decrease of at least 10%, 20%, 25%, 30%, 40%, 50%, 60%, 70%, 75%, 80%, 90% or up to 100% in the levels of synaptic protein synthesis or in the levels of β-arrestin2 mRNA or protein.

In some embodiments, the therapeutic compound includes an inhibitory molecule that alters β-arrestin2 mRNA splicing, stability, or translation. In some embodiments, the inhibitory molecule is a nucleic acid. Techniques for the inhibition of β-arrestin2 mRNA splicing or translation include, but are not limited to, the utilization of antisense oligomers consisting of DNA or RNA, or other synthetic structural types such as phosphorothioates, 2'-O-alkylribonucleotide chimeras, locked nucleic acids (LNA), peptide nucleic acids (PNA), or morpholinos. An "antisense oligomer" refers to an oligomer of at least about 10 nucleotides in length that is the complement of its targeted molecule (e.g., β-arrestin2 mRNA). In some embodiments the oligomer comprises at least 10, 11, 12, 13, 14, 15, 16, 17, 18, 19, 20, 21, 22, 23, 24, 25, 30, 35, 40, or 50 nucleotides. In some embodiments, the oligomers are completely complementary to their target. In other embodiments, the oligomers are at least about 70%, 75%, 80%, 85%, 90%, 91%, 92%, 93%, 94%, 95%, 96%, 97%, 98%, or 99% complimentary to their target. Antisense oligomers of the invention may be synthesized by standard methods known in the art. The antisense oligomers can also be expressed intracellularly from recombinant DNA introduced via genome editing techniques. The recombinant DNA comprises sequences encoding the antisense oligomers of the invention and any suitable promoter for expressing the antisense oligomer sequences. Selection of suitable promoters is within the skill in the art. The recombinant DNA of the invention can also comprise inducible or regulatable promoters for expression of the antisense oligomers in the tissue or cells where expression is desired (e.g. neuronal cells).

As used herein, an "effective amount" of an antisense oligomers is an amount sufficient to impede splicing or translation of the target mRNA, an amount sufficient to decrease synaptic protein synthesis, or an amount sufficient to ameliorate a subject's symptoms arising due to fragile X or a related disorder. Decreases in properly spliced target mRNA or target protein levels and in synaptic protein synthesis can be detected using standard techniques known in the art. One skilled in the art can readily determine an effective amount of antisense oligomer to be administered to a given subject. In some embodiments, treatment with antisense oligomers will result in a decrease of at least 10%, 20%, 25%, 30%, 40%, 50%, 60%, 70%, 75%, 80%, 90% or up to 100% in the levels of synaptic protein synthesis or in the levels of β-arrestin2 protein or properly spliced β-arrestin2 mRNA.

Techniques for the destabilization of β-arrestin2 mRNA include, but are not limited to, the utilization of ribozymes or RNAi (e.g., siRNA and shRNA). Ribozymes are catalytic RNA molecules with enzyme-like cleavage properties that can be designed to target specific RNA sequences. RNAi is a form of post-transcriptional gene silencing mediated by small interfering RNAs (siRNAs). Endogenous siRNAs are generated by ribonuclease III cleavage of longer dsRNAs (including shRNAs). shRNAs are RNA molecules that typically consist of a self-complementary double stranded region of 19-29 base pairs (the stem), a loop of at least 4 nucleotides, and a dinucleotide overhang at the 3' end. siRNAs, which are typically 20-25 nucleotide in length, comprise a sense RNA strand and a complementary antisense RNA strand annealed together by standard base pairing interactions. The sense strand comprises a nucleic acid sequence that is identical to a target sequence contained within the target mRNA (i.e., β-arrestin2). In some embodiments, the method utilizes siRNAs that are completely complementary. In other embodiments, the method utilizes siRNAs that comprise a sense and/or antisense strand containing a 3' or 5' overhang. An "overhang" refers to at least one unpaired nucleotide extending beyond the region of complementarity. In some embodiments, the method utilizes siRNAs (including siRNAs generated by shRNAs) that target any stretch of approximately 19 to 25 contiguous nucleotides in any of the β-arrestin2 mRNA sequences (the "target sequence"). Techniques for selecting target sequences for siRNA are well known in the art. The siRNAs can be obtained using a number of techniques known to those of skill in the art (e.g., chemically synthesized or recombinantly produced). shRNAs can be expressed intracellularly from recombinant DNA introduced via genome editing techniques. The recombinant DNA comprise sequences encoding the shRNAs of the invention and any suitable promoter for expressing the shRNA sequences. Selection of suitable promoters is within the skill in the art. The recombinant DNA of the invention can also comprise inducible or regulatable promoters for expression of the shRNA in the tissue or cells where expression is desired (e.g. neuronal cells).

As used herein, an "effective amount" of a ribozyme, siRNA, or shRNA is an amount sufficient to cause degradation of the target mRNA, an amount sufficient to decrease synaptic protein synthesis, or an amount sufficient to ameliorate a subject's symptoms arising due to fragile X or a related disorder. Ribozyme- or RNAi-mediated degradation of the target mRNA can be detected by measuring levels of the target mRNA or protein, using standard techniques known in the art. Decreases in synaptic protein synthesis can be detected using standard techniques known in the art. One skilled in the art can readily determine an effective amount of ribozyme, siRNA, or shRNA of the invention to be administered to a given subject. In some embodiments, treatment with a ribozyme, siRNA, or shRNA will result in a decrease of at least 10%, 20%, 25%, 30%, 40%, 50%, 60%, 70%, 75%, 80%, 90% or up to 100% in the levels of synaptic protein synthesis or in the levels of β-arrestin2 mRNA or protein levels.

In some embodiments, local β-arrestin2 protein levels are modulated via inhibiting the transport of β-arrestin2 to the area of interest (i.e., the synapse). In other embodiments, β-arrestin2 protein levels are modulated via targeting the protein for degradation. Relevant techniques include, but are not limited to, peptide-directed lysosomal degradation which has recently been shown to rapidly and reversibly knock-down endogenous proteins through chaperone-mediated autophagy (Fan et al., Nature Neuroscience (2014) 17(3):471-80). In some embodiments, the compound includes a peptide-directed lysosomal degradation molecule that directs lysosomal degradation of β-arrestin2 proteins.

As used herein, an "effective amount" of a peptide-directed lysosomal degradation molecule is an amount sufficient to cause degradation of the target protein, an amount sufficient to decrease synaptic protein synthesis, or an amount sufficient to ameliorate a subject's symptoms arising due to fragile X or a related disorder. Lysosomal-mediated degradation of the target protein can be detected by measuring levels of the target protein using standard techniques known in the art. Decreases in synaptic protein synthesis can be detected using standard techniques known in the art. One skilled in the art can readily determine an effective amount of a peptide-directed lysosomal degradation molecule to be administered to a given subject. In some embodiments, treatment with the a peptide-directed lysosomal degradation molecule will result in a decrease of at least 10%, 20%, 25%, 30%, 40%, 50%, 60%, 70%, 75%, 80%, 90% or up to 100% in the levels of synaptic protein synthesis or in the levels of β-arrestin2 protein.

In some embodiments, the therapeutic compound includes a molecule that inhibits the interaction between mGlu$_5$ and β-arrestin2 proteins. In some embodiments, the therapeutic compound includes a molecule that binds to a β-arrestin2 protein. In other embodiments, the compound includes a molecule that binds to a mGlu$_5$ protein. In the context of disrupting the interaction between proteins, relevant molecules include, but are not limited to antibodies (including intrabodies), aptamers, and small molecules.

Aptamers are single-stranded DNA/RNA oligonucleotides with characteristic 3D structures artificially selected from synthesized random-sequence nucleic acid libraries by in vitro evolution process such as SELEX (Systematic Evolution of Ligands by Exponential Enrichment). Aptamers are able to bind their targets with high affinity and specificity. Various aptamers targeting β-arrestin2 protein have been developed, including 5'-GGGAGGAC-GAUGCGGAUUCCGUUAAGUAUCGCGUUAAACGC-UAUGCGGACGC GUCAGACGACUCGCUGAGGAUC-CGAGA-3' (SEQ ID NO: 1), 5'-GGGAGGACGAUGCGGCCAGGUGUAGACA-GACGUGAGAGAUUGACCUGGCAGC AGCCAGAC-GACUCGCUGAGGAUCCGAGA-3' (SEQ ID NO: 2), or 5'-GGGAGGACGAUGCGGAUCCUCGUCCCGUCACG-GCAGAACCACGUCAGGCCUUC AACAGACGA-CUCGCUGAGGAUCCGAGA-3' (SEQ ID NO: 3) (Kotula et. al., PLoS One 4, e93441 (2014)).

The term "antibody" or "antibodies" relates to an antibody that specifically binds β-arrestin2 or mGlu$_5$. "Intrabodies" are antibodies expressed intracellularly to block cellular functions (see, e.g., Marschall and Dilbel, Comput Struct Biotechnol J. (2016)14:304-8). An antibody may be monoclonal or may be an antigen-binding fragment thereof: F(ab')2, F(ab) or single chain Fv type, or any type of recombinant antibody derived thereof. Technologies for generating antibodies and modifying them so that they are able to pass the blood-brain barrier are well known to the skilled person.

The term small molecule includes, but is not limited to small organic molecules and other drug candidates that can be obtained, for example, from combinatorial and natural product libraries. Techniques for identifying small molecules that disrupt the interaction between proteins are known in the art. There is little doubt that the identification of allosteric modulators of mGlu$_5$ or 0-arrestin that specifically impede the interaction between mGlu$_5$ and β-arrestin is feasible. Indeed, various known allosteric modulators of mGlu receptors impact only a fraction of all mGlu dependent signaling pathways (Hathaway et al., Neuropharmacology 93, 199-208 (2015); Iacovelli et al., Neuropharmacology 77, 303-12 (2014); Sheffler et al., Adv. Pharmacol. 62, 33-77 (2011)).

As used herein, an "effective amount" of an antibody, aptamer, or small molecule is an amount sufficient to decrease the interaction between mGlu$_5$ and β-arrestin2 proteins, an amount sufficient to decrease synaptic protein synthesis, or an amount sufficient to ameliorate a subject's symptoms arising due to fragile X or a related disorder. Decreases in the interaction between mGlu$_5$ and β-arrestin2 proteins and decreases in synaptic protein synthesis can be detected using standard techniques known in the art. One skilled in the art can readily determine an effective amount of antibody, aptamer, or small molecule to be administered to a given subject. In some embodiments, treatment with the an antibody, antibody, or small molecule will result in a decrease of at least 10%, 20%, 25%, 30%, 40%, 50%, 60%, 70%, 75%, 80%, 90% or up to 100% in the levels of synaptic protein synthesis or in the levels of the interaction between mGlu$_5$ and β-arrestin2 proteins.

In some embodiments, the therapeutic compound is administered orally, parenterally, intravenously, topically, intraperitoneally, subcutaneously, intracranially, intrathecally, or by inhalation. In some embodiments, the agent is administered by continuous infusion.

Selection of an appropriate route of administration will depend on various factors not limited to the particular disorder and/or severity of the disorder.

In some embodiments, the therapeutic compound is administered in one dose. In some embodiments, the compound is administered in multiple doses. In some embodiments, the therapeutic compound contains a cocktail of at least two molecules that inhibit β-arrestin2 protein levels and/or inhibit the interaction between mGlu$_5$ and β-arrestin2 proteins. In some embodiments, more than one compound (e.g., 2, 3, 4, 5, or more agents) are administered together in one dose. In some embodiments, more than one compound (e.g., 2, 3, 4, 5, or more agents) are administered in separate doses. In some embodiments, the multiple or separate doses are administered by the same route of administration (e.g., each dose is administered intravenously). In some embodiments, the multiple or separate doses are administered by different routes of administrations (e.g., one dose is administered intravenously and another dose(s) is administered orally).

In some embodiments the compound also comprises a pharmaceutical composition, which may routinely contain pharmaceutically acceptable concentrations of salt, buffering agents, preservatives, compatible carriers, adjuvants, pharmaceutically acceptable excipients, and optionally other therapeutic ingredients. The nature of the pharmaceutical carrier, excipient, and other components of the pharmaceutical composition will depend on the mode of administration. The pharmaceutical compositions of the disclosure may be administered by any means and route known to the skilled artisan in carrying out the treatment methods described herein.

Any of the therapeutic compounds, described herein, may be administered systemically. In some embodiments, the compound is formulated for parenteral administration by injection. Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form.

Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes.

Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In some embodiments, the therapeutic compound is formulated for oral administration. In some embodiments, the compound is formulated readily by combining the compounds with pharmaceutically acceptable carriers well known in the art. Such carriers enable the compounds of the disclosure to be formulated as tablets, pills, dragees, capsules, liquids, gels, syrups, slurries, suspensions and the like, for oral ingestion by a subject to be treated.

Pharmaceutical preparations for oral administration can be obtained as solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally, the oral formulations may also be formulated in saline or buffers (e.g., EDTA for neutralizing internal acid conditions) or may be administered without any carriers.

For oral delivery, the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films. A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic powder; for liquid forms, a soft gelatin shell may be used. The shell material of cachets could be thick starch or other edible paper. For pills, lozenges, molded tablets or tablet triturates, moist massing techniques can be used.

Any of the therapeutic compounds described herein may be provided in a formulation as fine multiparticulates in the form of granules or pellets. The formulation of the material for capsule administration could also be as a powder, lightly compressed plugs or even as tablets. The formulation could be prepared by compression. One may dilute or increase the volume of the formulation with an inert material. These diluents could include carbohydrates, especially mannitol, α-lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell. Disintegrants may be included in the formulation, such as in a solid dosage form. Materials used as disintegrants include but are not limited to starch, including the commercial disintegrant based on starch, Explotab®, sodium starch glycolate, Amberlite, sodium carboxymethylcellulose, ultramylopectin, sodium alginate, gelatin, orange peel, acid carboxymethyl cellulose, natural sponge and bentonite may also be used. Binders may be used to hold the compound together to form a hard tablet and include materials from natural products such as acacia, tragacanth, starch and gelatin. An anti-frictional agent may be included in the formulation to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Glidants that might improve the flow properties of the drug during formulation and to aid rearrangement during compression might be added. The glidants may include starch, talc, pyrogenic silica and hydrated silicoaluminate.

Also contemplated herein is pulmonary delivery of a therapeutic compound. The compound may be delivered to the lungs of a mammal for local or systemic delivery. For administration by inhalation, the therapeutic compound may be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). Also contemplated herein, is nasal delivery of a therapeutic compound with allows the passage of a pharmaceutical composition to the blood stream directly after administering the composition to the nose, without the necessity for deposition of the product in the lung.

In some embodiments, the therapeutic compound is administered locally. Local administration methods are known in the art and will depend on the target area or target organ. Local administration routes include the use of standard topical administration methods such by inhalation, intracranially, and/or intrathecally. In some embodiments, any of the compounds described herein may be delivered to the nervous system. In some embodiments, any of the compounds described herein may be delivered by intracranial injection. In some embodiments, any of the compounds described herein may be delivered through the spinal cord. The compounds may also be formulated in rectal or vaginal compositions such as suppositories or retention enemas (e.g., containing conventional suppository bases such as cocoa butter or other glycerides). In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble analogs, for example, as a sparingly soluble salt.

The therapeutic compounds also may comprise suitable solid or gel phase carriers or excipients. Examples of such carriers or excipients include but are not limited to calcium carbonate, calcium phosphate, various sugars, starches, cellulose analogs, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or one or more auxiliaries such as disintegrants, binders, coating agents, swelling agents, lubricants, flavorings, sweeteners or solubilizers are customarily used as described above. The pharmaceutical compositions are suitable for use in a variety of drug delivery systems. The compounds and compositions described herein may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

The pharmaceutical compositions of the disclosure may contain an effective amount of the compound with a pharmaceutically-acceptable carrier or excipient. The term pharmaceutically acceptable excipient means one or more compatible solid or liquid filler, diluents or encapsulating substances which are suitable for administration to a human or other vertebrate animal. The term excipient denotes an organic or inorganic ingredient, natural or synthetic, with which the active ingredient is combined to facilitate the application. The components of the therapeutic compositions also are capable of being commingled with the compounds of the present disclosure, and with each other, in a manner such that there is no interaction which would substantially impair the desired pharmaceutical efficiency.

Both non-biodegradable and biodegradable polymeric materials can be used in the manufacture of particles for delivering the compounds of the disclosure. Such polymers may be natural or synthetic polymers. The polymer is selected based on the period of time over which release is desired. Bioadhesive polymers of particular interest include bioerodible hydrogels. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(5 octadecyl acrylate). The therapeutic compounds described herein may be contained in controlled release systems. The term "controlled release" is intended to refer to any compounds and compositions described herein containing formulation in which the manner and profile of compounds and compositions described herein release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a compound over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the compound therefrom. "Delayed release" may or may not involve gradual release of a compound over an extended period of time, and thus may or may not be "sustained release." Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well known to those of ordinary skill in the art and include some of the release systems described above.

In some embodiments, the therapeutic compound is administered periodically. For example, the therapeutic compound can be administered more than once daily, once daily, twice weekly, once weekly, twice monthly, once monthly, every other month, and so on.

EXAMPLES

Methods and Materials
Animals

Arrb2$^{+/-}$ male and female mutant mice on the C57Bl/6J clonal background were bred together to produce the WT and Arrb2$^{+/-}$ offspring used in this study. Fmr1$^{-/x}$ female mice (Jackson Labs) were crossed with Arrb2$^{+/-}$ mice to generate double mutant animals. All experimental animals were age-matched male littermates, and were studied with the experimenter blind to genotype and treatment condition Animals were group housed and maintained on a 12:12 hour, light: dark cycle. The Institutional Animal Care and Use Committee at MIT approved all experimental techniques and all animals were treated in accordance with NIH and MIT guidelines.

Electrophysiology

Slices were prepared as described previously (Dolen et al., Neuron 6, 955-56 (2007)). Acute hippocampal slices (350 μm) were prepared from P28-35 animals in ice-cold dissection buffer containing (in mM): NaCl 87, Sucrose 75, KCl 2.5, NaH$_2$PO$_4$ 1.25, NaHCO$_3$ 25, CaCl$_2$ 0.5, MgSO$_4$ 7, Ascorbic acid 1.3, and D-glucose 10 (saturated with 95% O$_2$/5% CO$_2$). Immediately following slicing the CA3 region was removed. Slices were recovered in artificial cerebrospinal fluid (aCSF) containing (in mM): NaCl 124, KCl 5, NaH$_2$PO$_4$ 1.23, NaHCO$_3$ 26, CaCl$_2$ 2, MgCl$_2$ 1, and D-glucose 10 (saturated with 95% O$_2$/5% CO$_2$) at 32.5° C. for ≥3 hours prior to recording.

Field recordings were performed in a submersion chamber, perfused with aCSF (2-3 ml/min) at 30° C. Field EPSPs (fEPSPs) were recorded in CA1 stratum radiatum with extracellular glass electrodes (1-2 MΩ) filled with aCSF. Baseline responses were evoked by stimulation of the Schaffer collaterals at 0.033 Hz with a 2-contact cluster electrode (FHC) using a 0.2 ms stimulus yielding 40-60% of the maximal response. fEPSP recordings were filtered at 0.1 Hz-1 kHz, digitized at 10 kHz, and analyzed using pClamp9 (Axon Instruments). The initial slope of the response was used to assess changes in synaptic strength. Data were normalized to the baseline response and are presented as group means±SEM. The input output function was examined by stimulating slices with incrementally increasing current and recording the fEPSP response.

Paired pulse facilitation was induced by applying two pulses at different interstimulus intervals. Facilitation was measured by the ratio of the fEPSP slope of stimulus 2 to stimulus 1. NMDAR-dependent LTD was induced by delivering 900 test pulses at 1 Hz. mGlu-LTD was induced by (S)-3,5-Dihydroxyphenylglycine (DHPG, 25 μM) for 5 minutes. In order to determine the protein synthesis dependency of mGlu-LTD, slices were incubated with the protein synthesis inhibitor cycloheximide (60 μM) for at least 10 minutes prior to recording and throughout the entire experiment. The magnitude of LTD was measured by comparing the average response 55-60 minutes post DHPG/LFS application to the average of the last 5 minutes of baseline. Statistical significance for input-output function, paired-pulse facilitation, and mGlu- or NMDAR-dependent plasticity was determined by two-way ANOVA and post-hoc Student's t-tests.

Fluorescence-Based Calcium Imaging in Brain Slices

Hippocampal slices were prepared as described for electrophysiology experiments and recovered in aCSF for 2 hours at 32° C. Slices were then moved to a small recovery chamber and incubated in oxygenated aCSF containing 20 μM fluo-4-acetoxymethyl ester (fluo-4 AM; ThermoFisher) and 0.1% Pluronic F-127 (ThermoFisher) for 1 hour in the dark. After 1 hour, slices were then washed with oxygenated aCSF containing 1 μM tetrodotoxin (Abcam) and 50 μM D-AP5 (Tocris) for 20 minutes in a recording chamber. A low-powered (4×) objective was used to identify the brain region of interest. CA1 pyramidal neurons were visualized using a 40× water immersion objective and a Nikon Eclipse E600FN microscope.

Changes in Ca$^{2+}$ fluorescence were monitored in the presence of 1 μM tetrodotoxin and 50 μM D-AP5 using a Hamamatsu ORCA-100 camera, HCImage software (Hamamatsu), and a mercury arc-lamp and power supply (Nikon). After a 10 second baseline, 25 μM (S)-3,5-DHPG was bath applied. For a subset of experiments, slices were pre-treated with 10 μM U73122 during the wash period to block phospholipase C activity. Data were analyzed using Image J software. Increases in Ca$^{2+}$ mobilization in hippocampal neurons were reported as changes in relative fluorescence divided by the baseline fluorescence (ΔF/F).

Metabolic Labeling

Metabolic labeling of new protein synthesis was performed as previously described (Osterweil et al., J. Neurosci. 46, 15616-27 (2010)). Male P28-P32 littermate mice were anesthetized with isoflurane and the hippocampus was rapidly dissected into ice-cold aCSF (in mM: 124 NaCl, 3 KCl, 1.25 NaH$_2$PO$_4$, 26 NaHCO$_3$, 10 dextrose, 1 MgCl$_2$, 2 CaCl$_2$, saturated with 95% O$_2$ and 5% CO$_2$). Hippocampal slices (500 μm) were prepared using a Stoelting Tissue Slicer and transferred into 32.5° C. aCSF (saturated with 95% O$_2$ and 5% CO$_2$) within 5 mM. Slices were incubated in aCSF undisturbed for 3.5-4 h to allow for recovery of basal protein synthesis. Actinomycin D (25 μM) and vehicle or CDPPB (10 μM) was then added to the recovery chamber for 30 mM to inhibit transcription and stimulate mGlu receptors, respectively after which slices were transferred to fresh aCSF containing ~10 mCi/ml [$^{35}$S] Met/Cys (Perkin Elmer) for an additional 30 mM Slices were then homogenized, and labeled proteins isolated by TCA precipitation. Samples were read with a scintillation counter and subjected to a protein concentration assay (Bio-Rad). Data was analyzed as counts per minute per microgram of protein, normalized to the [$^{35}$S] Met/Cys aCSF used for incubation and the average incorporation of all samples analyzed and then normalized to percent wild-type for each experiment. Statistical significance was determined using unpaired t-tests.

Immunoblotting

Hippocampal slices were prepared and recovered as described in metabolic labeling experiments. Sets of slices were stimulated with CDPPB (10 μM) for 30 minutes and then flash frozen in liquid nitrogen immediately after stimulation, prior to processing. Yoked unstimulated slices were also processed to assess basal signaling levels Immunoblotting was performed according to established methods using primary antibodies to p-ERK1/2 (Thr202/Tyr204) (Cell Signaling Technology), ERK1/2 (Cell Signaling Technology), p-Akt (Ser473) (Cell Signaling Technology), Akt (Cell Signaling Technology), pS6 240/44 (Cell Signaling Technology) and S6 (Cell Signaling Technology). Protein levels were measured by densitometry (Quantity One), and quantified as the densitometric signal of phospho-protein divided by the total protein signal in the same lane.

Inhibitory Avoidance Extinction

Inhibitory avoidance (IA) experiments were performed as previously described (Pietraszek, et. al., Neuropharmacology 1, 73-85 (2005)). On the day of testing, P56-P76 animals were placed into the dark compartment of an IA training box (a two-chambered Perspex box consisting of a lighted safe side and a dark shock side separated by a trap door) for 30 seconds followed by 90 seconds in the light compartment for habituation. Following the habituation period, the door separating the two compartments was opened and animals were allowed to enter the dark compartment. Latency to enter following door opening was recorded ("baseline," time 0, 8-9a.m.); animals with baseline entrance latencies of greater than 120 seconds were excluded. After each animal stepped completely into the dark compartment with all four paws, the sliding door was closed and the animal received a single scrambled foot-shock (0.5 mA, 2.0 seconds) via electrified steel rods in the floor of the box. This intensity and duration of shock consistently caused animals to vocalize and jump. Animals remained in the dark compartment for 15 seconds following the shock and were then returned to their home cages. Six to seven hours following IA training, mice received a retention test ("post-acquisition," time 6 hours, 2 p.m.-3 p.m.). During post-acquisition retention testing, each animal was placed in the lit compartment as in training; after a 90 second delay, the door opened, and the latency to enter the dark compartment was recorded (cut-off time 537 seconds).

For inhibitory avoidance extinction (IAE) training, animals were allowed to explore the dark compartment of the box for 200 seconds in the absence of foot-shock (animals remaining in the lit compartment after the cutoff were gently guided, using an index card, into the dark compartment); following IAE training, animals were returned to their home cages. Twenty-four hours following initial IA training, mice received a second retention test ("post-extinction 1," time 24 hours, 8 a.m-9 a.m.). Animals were tested in the same way as at the six hour time point, followed by a second 200 second extinction trial in the dark side of the box; following training animals were again returned to their home cages. Forty-eight hours following avoidance training, mice received a third and final retention test ("post-extinction 2," time 48 hours, 8 a.m.-9 a.m.).

Audiogenic Seizures

AGS experiments were performed as previously described (Pietraszek, et. al., Neuropharmacology 1, 73-85 (2005)). Animals at P19-25 (immediately following weaning) were habituated to the behavioral chamber (28×17.5×12 cm transparent plastic box) for 1 minute prior to stimulus onset. AGS stimulus was a 125 dB at 0.25 m siren (modified personal alarm, RadioShack model 49-1010, powered from a DC converter). Seizures were scored for incidence during a 2-minute stimulus presentation or until animal reached AGS endpoint (wild running, status epilepticus, respiratory arrest or death were all scored as seizure activity).

Object Recognition

Object Recognition Task was adapted from experiments previously described. Animals at P56-70 were habituated to a 40 cm×40 cm×40 cm box during 2×15 minute sessions, spaced 1-2 hours apart. Animals were returned to their home cage in between sessions. 24 hours post habituation animals were exposed to two identical objects for 2×10 minute exploration sessions in the same box, spaced 1-2 hours apart Animals were required to explore each object for at least 10 seconds (for a total of at least 20 seconds) in the first session to be included in the subsequent sessions. 24 hours post object exploration, one object was replaced with a novel object and the animals were allowed to explore the objects for 10 minutes. Time spent sniffing was recording during this exploration period and was characterized by sniffing within 2 cm of each object or directly touching the objects. Time spent climbing or on top of the objects was not included. Familiar and novel object and side placement was randomly assigned, by animal Discrimination index was calculated as [(time spent exploring novel object)/(time spent exploring novel object+time spent exploring familiar object)].

MK801-Induced Hyperlocomotion

To determine the effects of genotype on MK801-induced hyperlocomotion, mice were habituated in the open field (40 cm×40 cm×40 cm box) for 60 min, followed by the administration of vehicle or MK801 and locomotor activity was recorded for another 60 mM. To determine the effects of MTEP by genotype on MK801-induced hyperlocomotion, mice were habituated in the open field for 30 min, followed by the intraperitoneal (i.p.) administration of MTEP (10 mg/kg at a dosing volume of 10 ml/kg). After an additional 30 mM, MK801 (0.3 mg/kg at a dosing volume of 10 ml/kg) was administered i.p. and locomotor activity was recorded for another 60 mM. The time course of drug-induced changes in ambulation was expressed as cm traveled/5 mM over the 120-min session. Sessions were recorded using Plexon's CINEPLEX® Studio and analyzed using Plexon's CINEPLEX® Editor and code written in MATLAB. MK801-induced locomotor activity was scored and analyzed using the average of the final 5 minutes (minute 115-120) per cohort.

Reagents (S)-3,5-dihydroxyphenylglycine (S-DHPG) was purchased from Tocris. Fresh bottles of DHPG were prepared as a 100× stock in $H_2O$, divided into aliquots, and stored at −80° C. Fresh stocks were made once a week. Cycloheximide (Sigma) was prepared daily at 100× stock in $H_2O$. Actinomycin D (Tocris) was prepared as a stock solution of 1 mg/mL in 0.01% DMSO and aCSF and stored at −20° C. CDPPB (Tocris) was prepared daily at 75 mM stock in DMSO. U73122 (Tocris) was prepared as a 5 mM stock in DMSO. MK801 (Sigma) was prepared in $H_2O$ daily and 0.3 mg/kg was injected i.p. at a dosing volume of 10 ml/kg. MTEP (Tocris) was prepared in $H_2O$ daily and 10 mg/kg was injected i.p. at a dosing volume of 10 ml/kg.

Figure 1B:
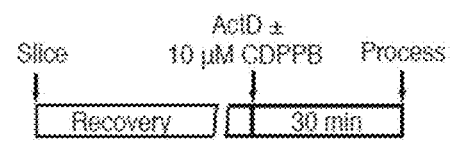
Figure 1B:
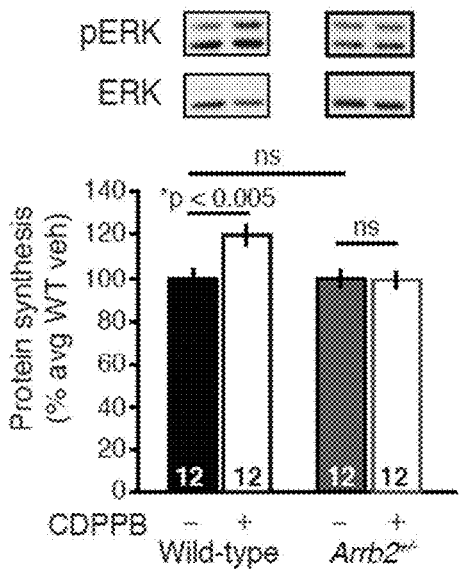
Figure 5A:
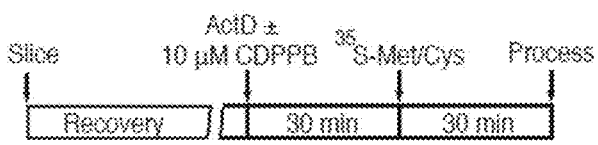
FIGS. 5A-5B. β-arrestin1 is not necessary for protein synthesis-dependent ERK1/2 activation.
Figure 5A:
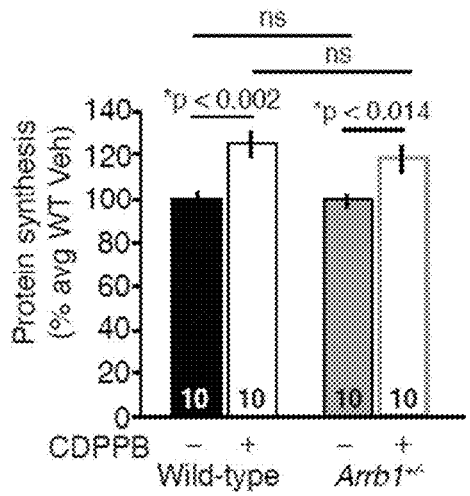
Figure 5B:
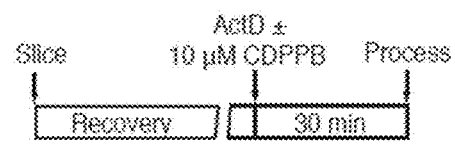
Figure 5B:
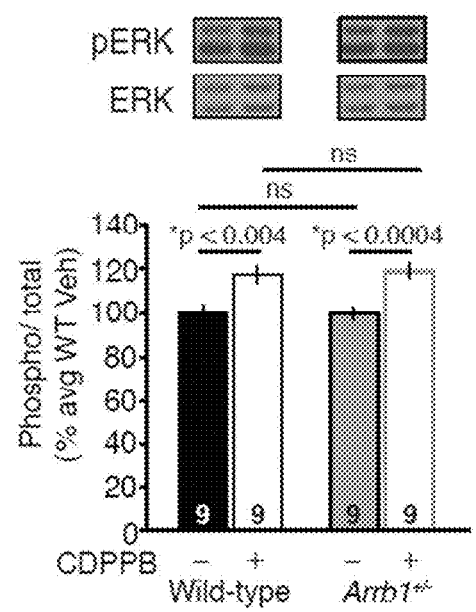
Figure 6A:
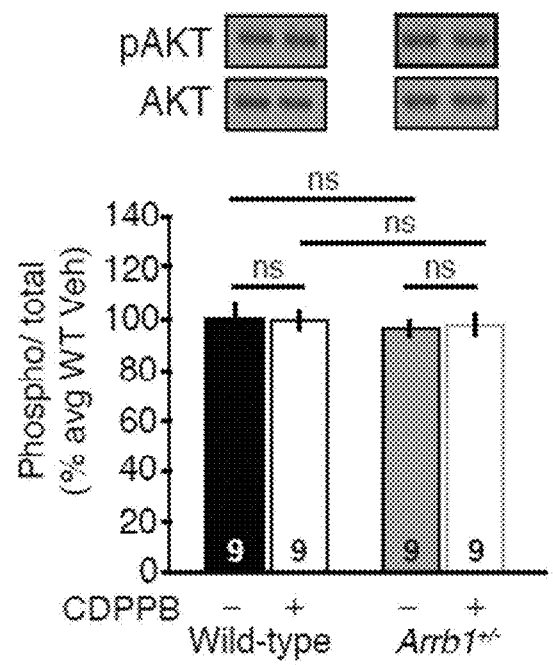
FIGS. 6A-6D. The AKT-mTOR pathway is not activated by CDPPB in wild-type, Arrb1$^{+/-}$ or Arrb2$^{+/-}$ mice.
Figure 6B:
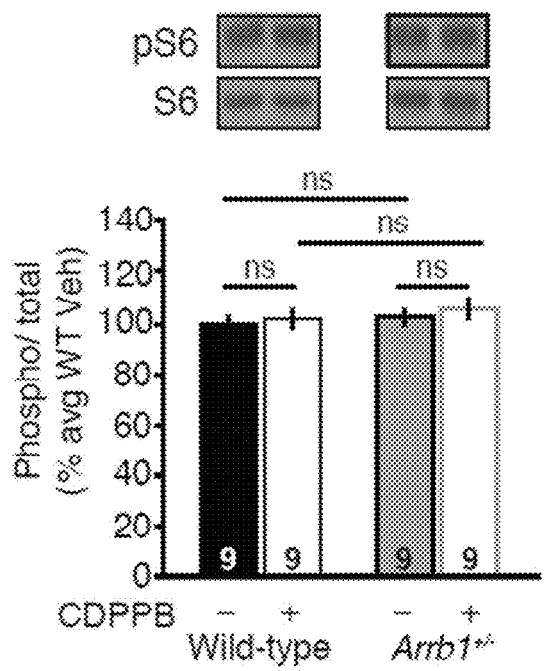
Figure 6C:
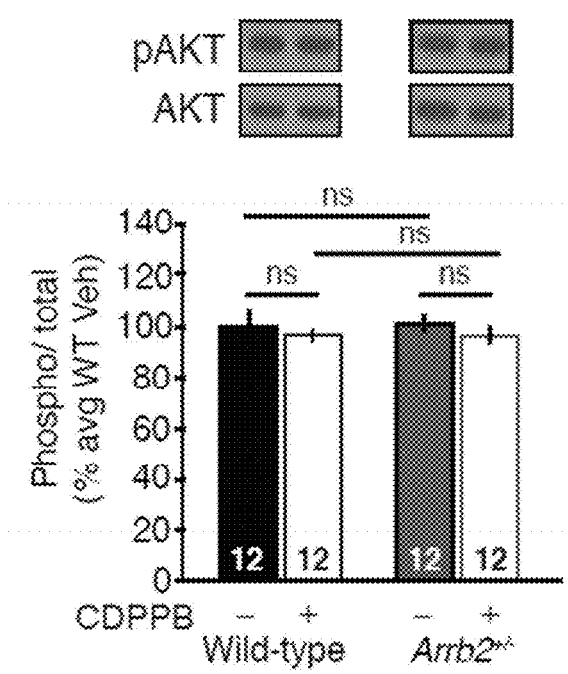
Figure 6D:
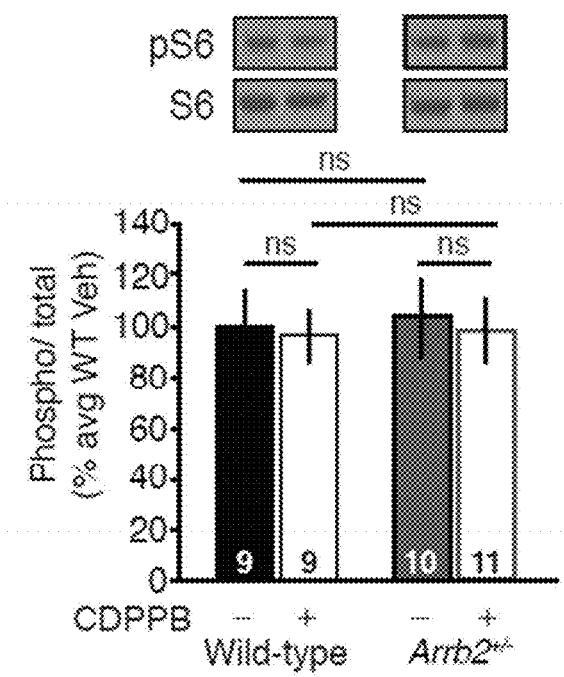
Figure 7A:
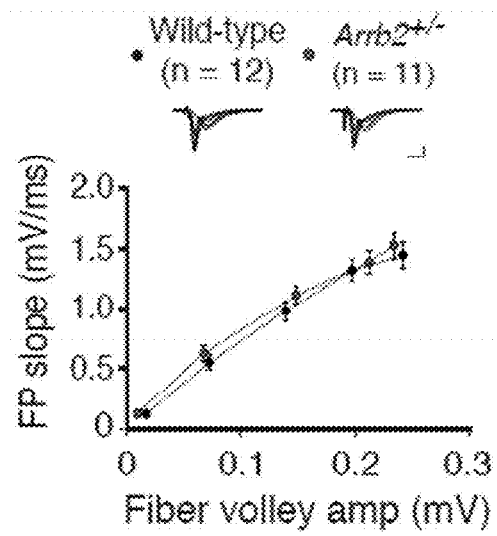
FIGS. 7A-7D. Arrb2$^{+/-}$ mice have normal basal synaptic function and NMDAR-dependent LTD.
Figure 7B:
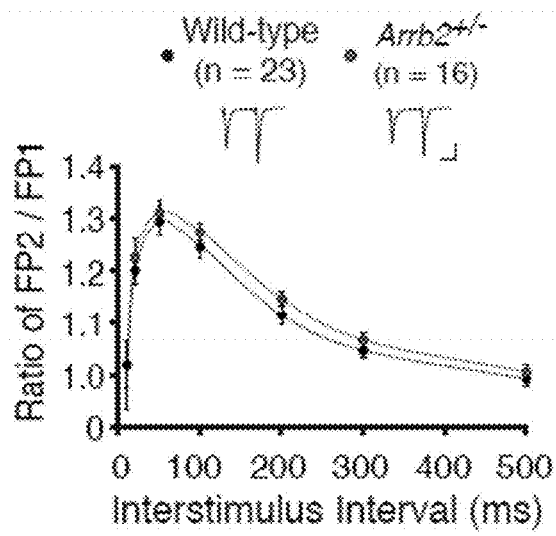
Figure 7C:
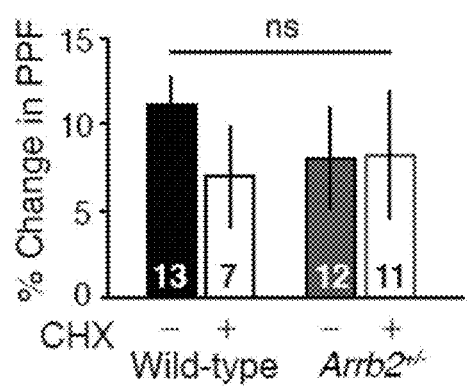
Figure 7D:
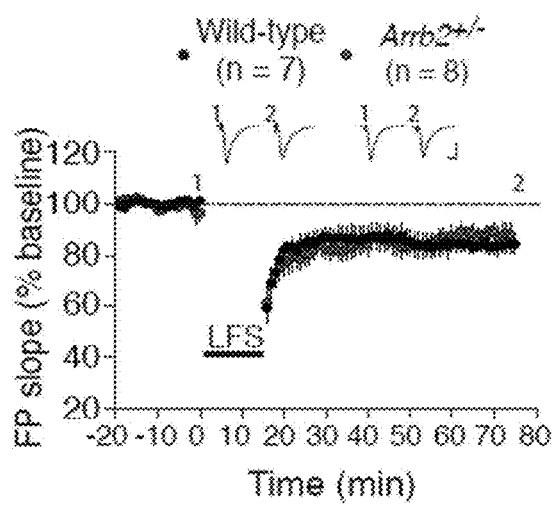

Example 1: Heterozygous Deletion of β-arrestin2 Disrupts mGlu$_5$ Stimulated ERK Activation and Protein Synthesis Without Affecting G$_a$-Signaling To determine the role of β-arrestin2 in mGlu$_5$-mediated protein synthesis, hippocampal slices from male Arrb2$^{+/-}$ and wild-type (WT) littermates were stimulated with a selective agonist and positive modulator of mGlu$_5$, 3-Cyano-N-(1,3-diphenyl-1H-pyrazol-5-yl) benzamide (CDPPB, 10 μM, 30 minutes), and the incorporation of $^{35}$S-methionine/cysteine into new protein was measured. mGlu$_5$ activation caused a parallel increase in protein synthesis (FIG. 1A) and ERK1/2 phosphorylation (FIG. 1B) in WT slices, which were both absent in slices from Arrb2$^{+/-}$ mice. This blunted response to mGlu$_5$ stimulation occurred in the absence of differences in basal protein synthesis rates or ERK phosphorylation levels (FIGS. 1A-1B). A comparable effect on stimulated protein synthesis in Arrb1$^{+/-}$ mice (FIGS. 5A-5B) was not observed, suggesting that β-arrestin2 is the relevant isoform for mGlu$_5$ signaling. From a therapeutic standpoint, it is noteworthy that mGlu$_5$-stimulated protein synthesis is abrogated in mice lacking a single allele of Arrb2; a full knockout is not required to see an effect.

β-arrestins have also been shown to participate in additional signaling cascades, including the Akt-mTOR pathway that has been implicated in the regulation of protein synthesis (DeWire et al., Ann. Rev. Physiol. 69, 483-510 (2007)). Consistent with previous studies in the hippocampal slice (Osterweil et al., J. Neurosci. 46, 15616-27 (2010)), however, mGlu$_5$ activation failed to increase phosphorylation of Akt or ribosomal protein S6, a readout of mTOR activity, in WT mice. These measures of mTOR pathway activity were also unaffected in slices prepared from Arrb1$^{+/-}$ and Arrb2$^{+/-}$ mice (FIGS. 6A-6D).

Figure 1C:
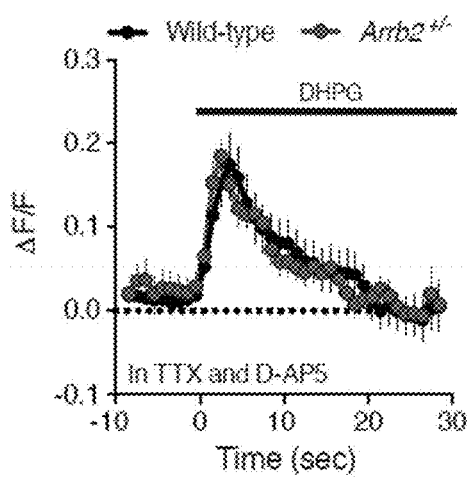
Figure 1D:
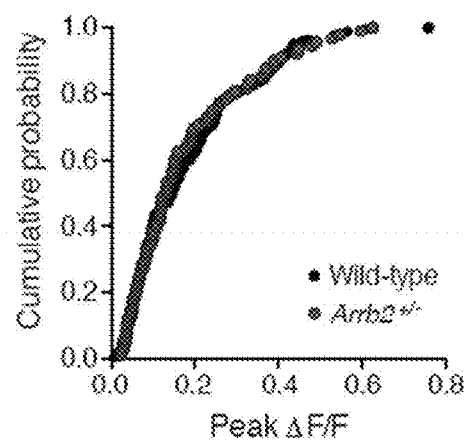

To assay the integrity of G$_q$ signaling, calcium mobilization in hippocampal slices from WT and Arrb2$^{+/-}$ animals was measured using the cell-permeable calcium fluorescent dye Fluo4-AM. A brief application of the agonist S-3,5-dihydroxyphenylglycine (DHPG, 25 μM, 1 min) to slices resulted in a rapid increase in Ca$^{2\pm}$-mediated fluorescence that was not significantly different between WT and Arrb2$^{+/-}$ slices (FIGS. 1C-1D). DHPG was employed in these experiments because it activates both of the G$_q$-coupled metabotropic glutamate receptors, mGlu$_1$ and mGlu$_5$. These DHPG-induced changes in calcium fluorescence were completely blocked by pretreatment with the phospholipase C inhibitor, U73122 (data not shown). These results indicate that a partial reduction in β-arrestin2 does not result in aberrant G$_q$ signaling in response to mGlu$_5$ activation. Moreover, they suggest that modulation of mGlu$_5$ receptor-mediated protein synthesis can be dissociated from G-protein dependent signaling via manipulation of β-arrestin2.

Example 2: Deficient mGlu$_5$-Mediated Translation Impairs Synaptic Plasticity in the Hippocampus of Arrb2$^{+/-}$ Mutants Activation of mGlu$_5$ results in a form of synaptic long-term depression (LTD) in the hippocampus that requires rapid de novo synaptic protein synthesis (Huber et al., Science 5469, 1254-57 (2000)). The functional relevance of the observed biochemistry was investigated by determining if genetic reduction of Arrb2 also alters the expression and/or protein synthesis-dependency of LTD induced with DHPG (25 μM, 5 min) (Huber et al, J. Neurophysiol. 1, 321-25 (2001)). Basal synaptic transmission was normal (FIGS. 7A-7D), but LTD magnitude was significantly reduced in Arrb2$^{+/-}$ slices compared to WT (FIGS. 1E-1F). Consistent with previous observations, LTD in WT slices was significantly diminished in the presence of the protein synthesis inhibitor cycloheximide (CHX, 60 μM). In contrast, the residual LTD in slices from Arrb2$^{+/-}$ animals was unaffected by CHX (FIGS. 1E-1F). Therefore, the protein synthesis-dependent component of mGlu$_5$-mediated LTD is absent in the Arrb2$^{+/-}$ hippocampus.

In WT mice, the LTD that remains when DHPG is applied in the presence of CHX is expressed via a presynaptic mechanism, revealed by a change in the paired-pulse ratio (Auerbach et al., Nature 7375, 63-8 (2011)). This change in paired-pulse ratio after DHPG was similar in Arrb2$^{+/-}$ mice, indicating that this presynaptic, protein synthesis-independent mechanism of LTD is unaffected by reducing signaling through β-arrestin2 (FIGS. 7A-7D). Another, mechanistically distinct form of hippocampal LTD can be induced by stimulating NMDA receptors. This type of LTD is expressed postsynaptically, but does not require ERK1/2 or immediate translation of mRNA. It is also unaffected by genetic reduction of β-arrestin2 in the hippocampus (FIGS. 7A-7D). Taken together, these results suggest that the diminished LTD magnitude observed in Arrb2$^{+/-}$ animals is likely a specific consequence of impaired mGlu$_5$-stimulated mRNA translation at the synapse.

Figure 2A:
FIGS. 2A-2D. Genetic reduction of β-arrestin2 in Fmr1$^{-/y}$ mice corrects exaggerated protein synthesis and mGlu-LTD.
Figure 2B:
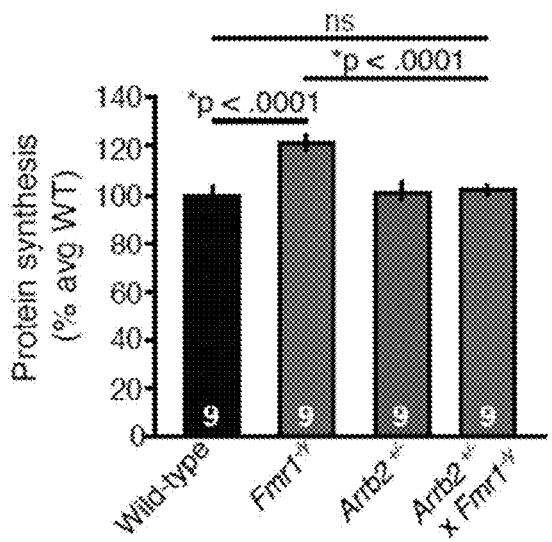
Figure 2C:
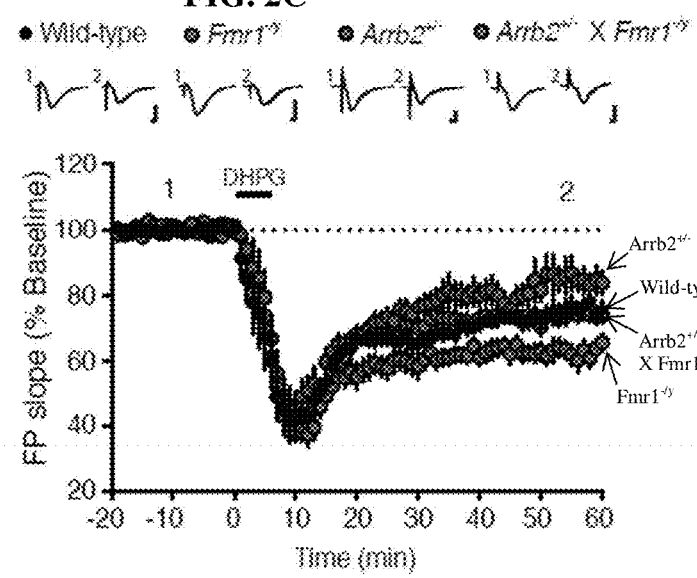
Figure 2D:
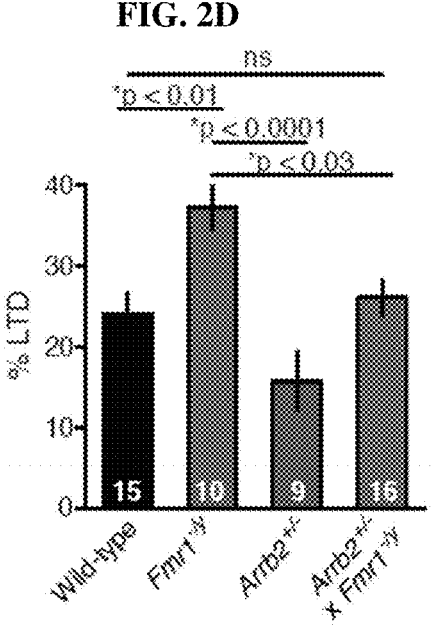

Example 3: Decreasing β-arrestin2 Levels Reverses Synaptic and Behavioral Deficits in a Mouse Model of Fragile X The results of Examples 1 and 2 indicate that β-arrestin2 couples mGlu$_5$ activation to ERK-dependent protein synthesis and LTD. Aberrantly increased mGlu$_5$-dependent protein synthesis has been shown to be pathogenic in Fmr1-null mice (Bhakar et al., Ann. Rev. Neurosci. 45, 417-43 (2012); Dolen et al., Neuron 6, 955-56 (2007)). Therefore, the determination of whether a genetic reduction of Arrb2 in Fmr1-null mice could correct FX phenotypes was investigated. Arrb2$^{+/-}$ male mice were crossed to Fmr1$^{x/-}$ female mice. Interestingly, both the increased synaptic protein synthesis (FIGS. 2A-2B) and exaggerated mGlu-LTD (FIGS. 2C-2D) characteristic of Fmr1$^{-/y}$ mice were restored to WT levels in Arrb2$^{+/-}$×Fmr1$^{-/y}$ mice.

Figure 3A:
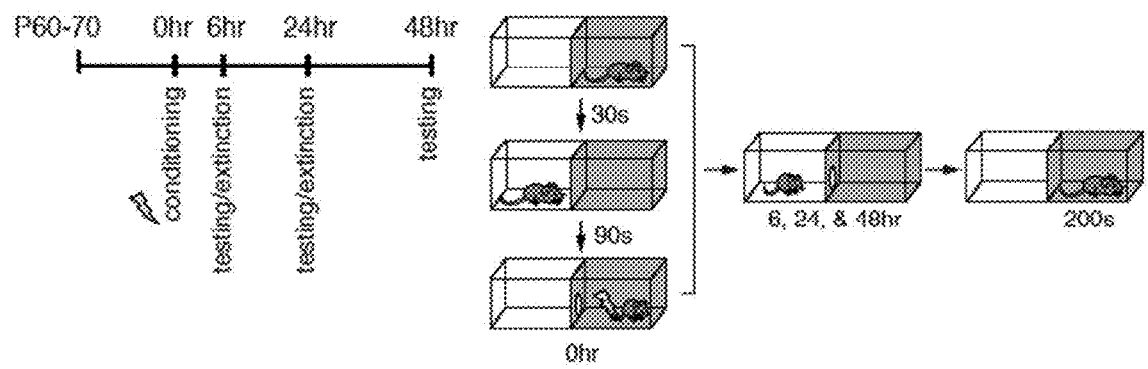
Figure 3B:
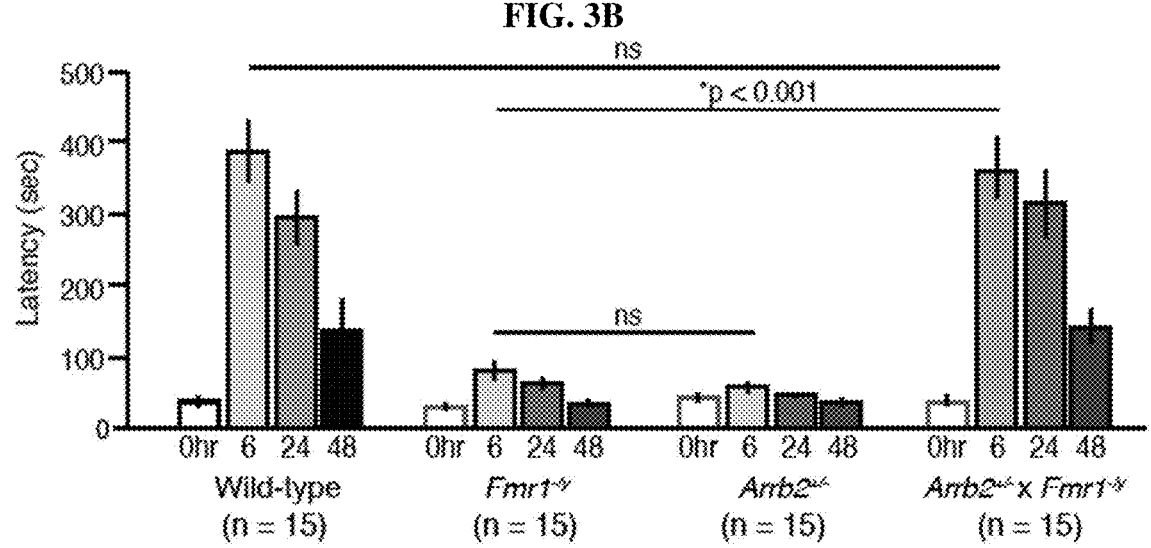

The possibility that restoration of normal protein synthesis and mGlu$_5$-dependent synaptic plasticity could lead to improvements in cognitive and behavioral assays previously shown to be impaired in Fmr1$^{-/y}$ mice was investigated next. Inhibitory avoidance, a hippocampus-dependent behavior known to be disrupted in Fmr1$^{-/y}$ mice, was assayed (Dolen et al., Neuron 6, 955-56 (2007); Qin et al., Pro. Natl. Acad. Sci. U.S.A. 24, 15758-63 (2002)) (FIG. 3A). Memory strength was measured as the latency to enter the dark side of a box that was associated with a foot shock. Arrb2$^{+/-}$ as well as Fmr1$^{-/y}$ mice failed to form a strong association between the context and foot shock (between time 0 and 6 hours) indicating impaired memory acquisition. This is consistent with previous results showing that both excessive and deficient hippocampal synaptic protein synthesis can manifest similarly at the behavioral level (Auerbach et al., Nature 7375, 63-8 (2011)). Remarkably, however, Arrb2$^{+/-}$× Fmr1$^{-/y}$ mice were indistinguishable from WT and exhibited normal memory acquisition and extinction over the course of 48 hours (FIG. 3B).

Non-aversive object recognition memory was also investigated. Mice were first allowed to explore an arena with two identical objects for two sessions. The following day, one of the familiar objects was replaced with a novel object (FIG. 3C). While Fmr1$^{-/y}$ mice explored both the novel and familiar objects to an equal degree, indicating a severe impairment in novelty detection, Arrb2$^{+/-}$×Fmr1$^{-/y}$ mice as well as Arrb2$^{+/-}$ single mutants showed a strong preference for the novel object similar to WT mice (FIG. 3D).

In an additional series of behavioral experiments, audiogenic seizures (AGS) were investigated, as increased susceptibility to AGS is a hallmark phenotype in Fmr1$^{-/y}$ mice. Genetic reduction of Arrb2 in Fmr1-null mice significantly attenuated seizure incidence (FIG. 3E), very similar to what has been observed using mGlu$_5$ and ERK-pathway inhibitors (Dolen et al., Neuron 6, 955-56 (2007); Osterweil et al., J. Neurosci. 46, 15616-27 (2010); Yan et al., Neuropharmacology 7, 1053-66 (2005)).

Figure 4:
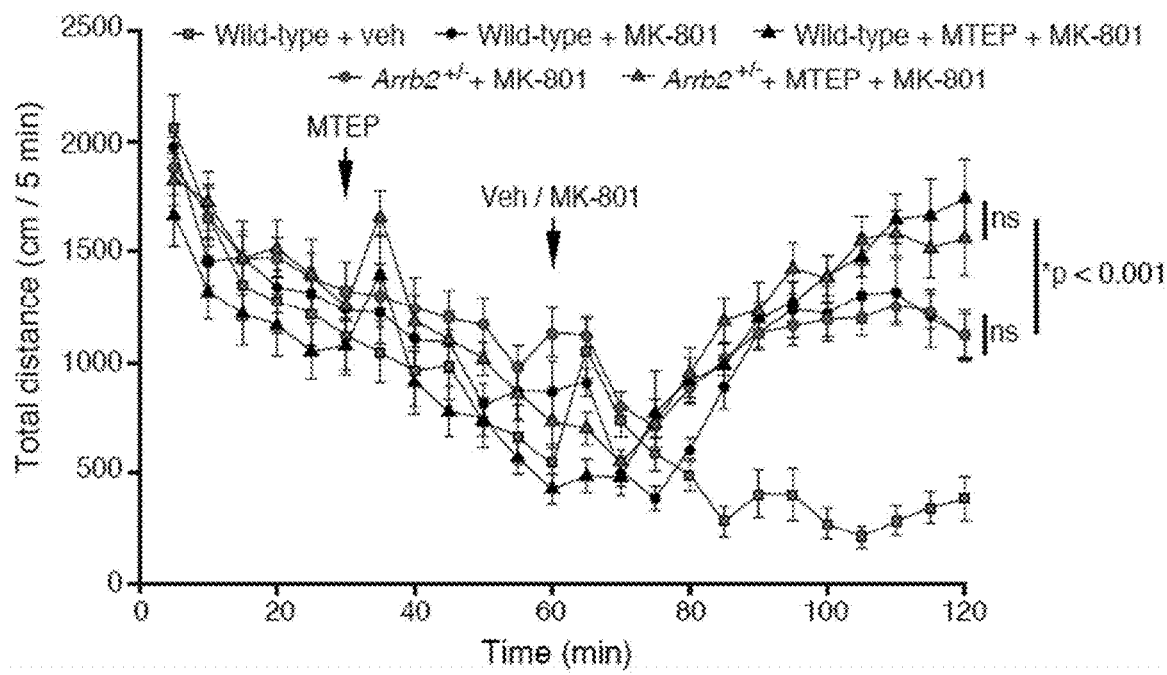
FIG. 4. Genetic reduction of β-arrestin2 does not potentiate the psychotomimetic effects of MK801. WT and Arrb2$^{+/-}$ mice injected intraperitoneally with the NMDAR antagonist MK801 (0.3 mg/kg) show comparable hyperlocomotion 60 minutes post-treatment compared to vehicle (N=10 mice per group). Data points represent distance travelled in cm over 5 minute bins, averaged as pooled animals per treatment group. Pre-treatment with MTEP (10 mg/kg, i.p.) potentiates hyperlocomotion in both WT and Arrb2$^{+/-}$ mice (N=9 mice per group). Two-way ANOVA for genotype: p=0.499 and for treatment: *p<0.001, no significant interaction between genotype and treatment. Student's two-tailed t-test wild-type +MK801 vs. wild-type+MTEP+ MK801: *p=0.009. Student's two-tailed t-test Arrb2$^{+/-}$+ MK801 vs. Arrb2$^{+/-}$+MTEP+MK801 *p=0.037.

Example 4: Unlike First Generation mGlu$_5$ NAMs, β-arrestin2 Reduction does not Exacerbate MK-801-Induced Hyperlocomotion The results of Examples 1-3 indicate that the mGlu$_5$ signaling relevant to FX pathophysiology passes through β-arrestin2 to activate ERK and protein synthesis. If this conclusion is correct, then modulators that specifically target mGlu$_5$ coupling to β-arrestin2 might avoid side effects that arise from inhibition of G$_q$ and/or mTOR pathway signaling. First-generation mGlu$_5$ NAMs were all identified based on inhibition of G$_q$ signaling, and in humans one adverse side effect reported following treatment with these compounds is derealization and visual hallucinations (Abou Farha et al., ISRN Psychiatry, 652750 (2014); Pecknold et al., J. Cli. Psychopharmacology 2, 129-33 (1982); Porter et al., J. Pharmacol. Exp. Ther. 2, 711-21 (2005)). Similarly in mice, mGlu$_5$ NAMs exacerbate hyperlocomotion in response to treatment with the potent psychotomimetic MK801 (Homayoun et al., Neuropsychopharmacology 7, 1259-69 (2004); Pietraszek et al., Neuropharmacology 1, 73-85 (2005)). Therefore the effect of genetic reduction of β-arrestin2 and mGlu$_5$ NAM treatment on MK801-induced hyperlocomotion in mice was examined. Pretreatment with the selective mGlu$_5$ inhibitor 3-[(2-Methyl-1,3-thiazol-4-yl) ethynyl]-pyridine (MTEP) (Cosford et al., J. Med. Chem. 2, 204-5 (2003)) significantly potentiates MK801-induced hyperlocomotion in WT mice. However, baseline locomotor activity was the same in Arrb2$^{+/-}$ and WT mice, as was the synergistic effect of MTEP pretreatment on MK801-induced hyperlocomotion (FIG. 4). The fact that MTEP continues to exacerbate hyperlocomotion in Arrb2$^{+/-}$ mice that lack mGlu$_5$-regulated protein synthesis suggests that the psychotomimetic effects of the NAM are mediated by inhibition of pathways unrelated to FX pathophysiology.

REFERENCES

1. Abou Farha K., Bruggeman R., and Balje-Volkers C. Metabotropic glutamate receptor 5 negative modulation in phase I clinical trial: potential impact of circadian rhythm on the neuropsychiatric adverse reactions-do hallucinations matter? ISRN Psychiatry, 2014: 652750.
2. Aguilar-Valles A., Matta-Camacho E., Khoutorsky A., Gkogkas C., Nader K., Lacaille J. C., and Sonenberg N., Inhibition of Group I Metabotropic Glutamate Receptors Reverses Autistic-Like Phenotypes Caused by Deficiency of the Translation Repressor eIF4E Binding Protein 2. J. Neurosci., 2015. 35(31): p. 11125-32.
3. Ahn S., Kim J., Hara M. R., Ren X. R., and Lefkowitz R. J., {beta}-Arrestin-2 Mediates Anti-apoptotic Signaling through Regulation of BAD Phosphorylation. J. Biol. Chem., 2009. 284(13): p. 8855-65.
4. Auerbach B. D., Osterweil E. K., and Bear M. F., Mutations causing syndromic autism define an axis of synaptic pathophysiology. Nature, 2011. 480(7375): p. 63-8.
5. Banko J. L., Hou L., Poulin F., Sonenberg N., and Klann E., Regulation of eukaryotic initiation factor 4E by converging signaling pathways during metabotropic glutamate receptor-dependent long-term depression. J. Neurosci., 2006. 26(8): p. 2167-73.
6. Barnes S. A., Wijetunge L. S., Jackson A. D., Katsanevaki D., Osterweil E. K., Komiyama N. H., Grant S. G., Bear M. F., Nagerl U. V., Kind P. C., and Willie D. J., Convergence of Hippocampal Pathophysiology in Syngap+/− and Fmr1−/y Mice. J. Neurosci., 2015. 35(45): p. 15073-81.
7. Berry-Kravis E., Des Portes V., Hagerman R., Jacquemont S., Charles P., Visootsak J., Brinkman M., Rerat K., Koumaras B., Zhu L., Barth G. M., Jaecklin T., Apostol G., and von Raison F., Mavoglurant in fragile X syndrome: Results of two randomized, double-blind, placebo-controlled trials. Sci. Transl. Med., 2016. 8(321): 321ra5.
8. Bhakar A. L., Dolen G., and Bear M. F., The pathophysiology of fragile X (and what it teaches us about synapses). Ann. Rev. Neurosci., 2012. 35: p. 417-43.
9. Bozdagi O., Sakurai T., Papapetrou D., Wang X., Dickstein D. L., Takahashi N., Kajiwara Y., Yang M., Katz A. M., Scattoni M. L., Harris M. J., Saxena R., Silverman J. L., Crawley J. N., Zhou Q., Hof P. R., and Buxbaum J. D., Haploinsufficiency of the autism-associated Shank3 gene leads to deficits in synaptic function, social interaction, and social communication. Mol. Autism, 2010. 1(1): p. 15.
10. Cosford N. D., Tehrani L., Roppe J., Schweiger E., Smith N. D., Anderson J., Bristow L., Brodkin J., Jiang X., McDonald I., Rao S., Washburn M., and Varney M. A. 3-[(2-Methyl-1,3-thiazol-4-yl)ethynyl]-pyridine: a potent and highly selective metabotropic glutamate subtype 5 receptor antagonist with anxiolytic activity. J. Med. Chem., 2003. 46(2): p. 204-6.
11. DeWire, S. M., Ahn, S., Lefkowitz, R. J., and Shenoy, S. K., Beta-arrestins and cell signaling. Ann. Rev. Physiol., 2007. 69: p. 483-510.
12. DeWire, S. M., Kim, J., Whalen, E. J., Ahn, S., Chen, M., and Lefkowitz, R. J., Beta-arrestin-mediated signaling regulates protein synthesis. J. Biol. Chem., 2008. 283(16): p. 10611-20.
13. Dolen, G., Osterweil, E., Rao, B. S., Smith, G. B., Auerbach, B. D., Chattarji, S., and Bear, M. F., Correction of fragile X syndrome in mice. Neuron, 2007. 56(6): p. 955-56.
14. Gallagher, S. M., Daly, C. A., Bear, M. F., and Huber, K. M., Extracellular signal-regulated protein kinase activation is required for metabotropic glutamate receptor-dependent long-term depression in hippocampal area CA1. J. Neurosci., 2004, 24(20): p. 4859-64.
15. Gasparini, F., Lingenhohl, K., Stoehr, N., Flor, P. J., Heinrich, M., Vranesic, I., Biollaz, M., Allgeier, H., Heckendorn, R., Urwyler, S., Varney M. A., Johnson E. C., Hess S. D., Rao S. P., Sacaan A. I., Santori E. M., Velicelebi G., and Kuhn R., 2-Methyl-6-(phenylethynyl)-pyridine (MPEP), a potent, selective and systemically active mGlu$_5$ receptor antagonist. Neuropharmacology, 1999. 38(10): p. 1493-503.
16. Hathaway, H. A., Pshenichkin, S., Grajkowska, E., Gelb, T., Emery, A. C., Wolfe, B. B., and Wroblewski, J. T., Pharmacological characterization of mGlu1 receptors in cerebellar granule cells reveals biased agonism. Neuropharmacology, 2015. 93: p. 199-208.
17. Homayoun, H., Stefani, M. R., Adams, B. W., Tamagan, G. D., and Moghaddam, B., Functional Interaction Between NMDA and mGlu$_5$ Receptors: Effects on Working Memory, Instrumental Learning, Motor Behaviors, and Dopamine Release. Neuropsychopharmacology, 2004. 29(7): p. 1259-69.
18. Huber, K. M., Kayser, M. S., and Bear, M. F., Role for rapid dendritic protein synthesis in hippocampal mGluR-dependent long-term depression. Science, 2000. 288 (5469): p. 1254-57.
19. Huber, K. M., Roder, J. C., and Bear, M. F., Chemical induction of mGluR5- and protein synthesis—dependent long-term depression in hippocampal area CA1. J Neurophysiol., 2001. 86(1): p. 321-25.
20. Iacovelli, L., Felicioni, M., Nistico, R., Nicoletti, F., and De Blasi, A., Selective regulation of recombinantly expressed mGlu7 metabotropic glutamate receptors by G protein-coupled receptor kinases and arrestins. Neuropharmacology, 2014. 77: p. 303-12.
21. Insel, P. A., Tang, C. M., Hahntow, I., and Michel, M. C., Impact of GPCRs in clinical medicine: monogenic diseases, genetic variants and drug targets. Biochim Biophys. Acta., 2007. 1768(4): p. 994-1005.
22. Kotula J. W., Sun J., Li M., Pratico E. D., Fereshteh M. P., Ahrens D. P., Sullenger B. A., and Kovacs J. J., Targeted disruption of β-arrestin 2-mediated signaling pathways by aptamer chimeras leads to inhibition of leukemic cell growth. PLoS One, 2014 9(4): e93441.
23. Lindemann, L., Jaeschke, G., Michalon, A., Vieira, E., Honer, M., Spooren, W., Porter, R., Hartung, T., Kolczewski, S., Buttelmann, B., Flament C., Diener C., Fischer C., Gatti S., Prinssen E. P., Parrott N., Hoffmann G., and Wettstein J. G., CTEP: a novel, potent, long-acting, and orally bioavailable metabotropic glutamate receptor 5 inhibitor. J. Pharmacol. Exp. Ther., 2011. 339(2): p. 474-86.
24. Osterweil, E. K., Chuang, S. C., Chubykin, A. A., Sidorov, M., Bianchi, R., Wong, R. K., and Bear, M. F., Lovastatin corrects excess protein synthesis and prevents epileptogenesis in a mouse model of fragile X syndrome. Neuron, 2013. 77(2): p. 243-50.
25. Osterweil, E. K., Krueger, D. D., Reinhold, K., and Bear, M. F., Hypersensitivity to mGluR5 and ERK1/2 leads to excessive protein synthesis in the hippocampus of a mouse model of fragile X syndrome. J. Neurosci., 2010. 30(46): p. 15616-27.
26. Pecknold, J. C., McClure, D. J., Appeltauer, L., Wrzesinski, L., and Allan, T., Treatment of anxiety using fenobam (a nonbenzodiazepine) in a double-blind standard (diazepam) placebo-controlled study. J. Cli. Psychopharmacology, 1982. 2(2): p. 129-33.
27. Pietraszek, M., Gravius, A., Schafer, D., Weil, T., Trifanova, D., and Danysz, W., mGluR5, but not mGluR1, antagonist modifies MK-801-induced locomotor activity and deficit of prepulse inhibition. Neuropharmacology, 2005. 49(1): p. 73-85.
28. Pop, A. S., Gomez-Mancilla, B., Neri, G., Willemsen, R., and Gasparini, F., Fragile X syndrome: a preclinical review on metabotropic glutamate receptor 5 (mGluR5) antagonists and drug development. Psychopharmacology, 2014. 231(6): p. 1217-26.
29. Porter, R. H., Jaeschke, G., Spooren, W., Ballard, T. M., Buttelmann, B., Kolczewski, S., Peters, J. U., Prinssen, E., Wichmann, J., Vieira, E., Mühlemann A., Gatti S., Mutel V., and Malherbe P., Fenobam: a clinically validated nonbenzodiazepine anxiolytic is a potent, selective, and noncompetitive mGlu$_5$ receptor antagonist with inverse agonist activity. J. Pharmacol. Exp. Ther., 2005. 315(2): p. 711-21.
30. Qin, M., Kang, J., and Smith, C. B., Increased rates of cerebral glucose metabolism in a mouse model of fragile X mental retardation. Proc. Natl. Aca. Sci. U.S.A., 2002. 99(24): 15758-63.
31. Richter, J. D., Bassell, G. J., and Klann, E., Dysregulation and restoration of translational homeostasis in fragile X syndrome. Nat. Rev. Neurosci., 2015. 16(10): p. 595-605.
32. Scharf, S. H., Jaeschke, G., Wettstein, J. G., and Lindemann, L., Metabotropic glutamate receptor 5 as drug target for Fragile X syndrome. Curr. Opin. Pharmacol., 2015. 20: p. 124-34.
33. Schnabel, R., Kilpatrick, I. C., and Collingridge, G. L., An investigation into signal transduction mechanisms involved in DHPG-induced LTD in the CA1 region of the hippocampus. Neuropharmacology, 1999. 38(10): p. 1585-96.
34. Sheffler, D. J., Gregory, K. J., Rook, J. M., and Conn, P. J., Allosteric modulation of metabotropic glutamate receptors. Adv. Pharmacol., 2011. 62: p. 37-77.
35. Tian, D., Stoppel, L. J., Heynen, A. J., Lindemann, L., Jaeschke, G., Mills, A. A., and Bear, M. F., Contribution of mGluR5 to pathophysiology in a mouse model of human chromosome 16p11.2 microdeletion. Nat. Neurosci., 2015. 18(2): p. 182-84.
36. Wenger, T. L., Kao, C., McDonald-McGinn, D. M., Zackai, E. H., Bailey, A., Schultz, R. T., Morrow, B. E., Emanuel, B. S., and Hakonarson, H., The Role of mGluR Copy Number Variation in Genetic and Environmental Forms of Syndromic Autism Spectrum Disorder. Sci. Rep., 2016. 6: 19372.
37. Whalen, E. J., Raj agopal, S., and Lefkowitz, R. J., Therapeutic potential of beta-arrestin- and G protein-biased agonists. Trends Mol. Med., 2011. 17(3): p. 126-39.
38. Yan, Q. J., Rammal, M., Tranfaglia, M., and Bauchwitz, R. P., Suppression of two major Fragile X Syndrome mouse model phenotypes by the mGluR5 antagonist MPEP. Neuropharmacology, 2005. 49(7): p. 1053-66.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B," when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B," the disclosure also contemplates the alternative embodiments "a composition consisting of A and B" and "a composition consisting essentially of A and B."

The invention claimed is:

1. A method of treating fragile X syndrome, fragile X-associated tremor/ataxia syndrome, an autism spectrum disorder, or tuberous sclerosis, comprising administering to a subject in need thereof an effective amount of a compound that reduces β-arrestin2 protein levels in said subject.

2. The method of claim 1, wherein the reduction of β-arrestin2 protein levels ameliorates increased protein synthesis, altered synaptic plasticity, or behavioral impairments in the fragile X syndrome, fragile X-associated tremor/ataxia syndrome, an autism spectrum disorder, or tuberous sclerosis.

3. The method of claim 1, wherein the subject in need thereof suffers from fragile X syndrome.

4. The method of claim 1, wherein the compound knocks out or disrupts the β-arrestin2 gene.

5. The method of claim 4, wherein the compound comprises a zinc finger nuclease, a transcription activator-like effector nuclease (TALEN), a meganuclease, or a CRISPR/Cas9 system.

6. The method of claim 1, wherein the compound comprises a molecule that alters β-arrestin2 mRNA splicing, stability, or translation.

7. The method of claim 6, wherein the compound comprises an inhibitory nucleic acid molecule.

8. The method of claim 7, wherein the inhibitory nucleic acid molecule is an antisense nucleic acid, a locked nucleic acid molecule, a peptide nucleic acid molecule, a morpholino, a siRNA molecule, a shRNA molecule or a ribozyme.

9. The method of claim 1, wherein the compound is administered periodically.

* * * * *

SEQUENCE LISTING

```
<160> NUMBER OF SEQ ID NOS: 3

<210> SEQ ID NO 1
<211> LENGTH: 79
<212> TYPE: RNA
<213> ORGANISM: Artificial Sequence
<220> FEATURE:
<223> OTHER INFORMATION: Aptamer

<400> SEQUENCE: 1
gggaggacga ugcggauucc guuaaguauc gcguuaaacg cuaugcggac gcgucagacg      60
acucgcugag gauccgaga                                                  79
```

```
<210> SEQ ID NO 2
<211> LENGTH: 80
<212> TYPE: RNA
<213> ORGANISM: Artificial Sequence
<220> FEATURE:
<223> OTHER INFORMATION: Aptamer

<400> SEQUENCE: 2
gggaggacga ugcggccagg uguagacaga cgugagagau ugaccuggca gcagccagac    60
gacucgcuga ggauccgaga                                                80

<210> SEQ ID NO 3
<211> LENGTH: 80
<212> TYPE: RNA
<213> ORGANISM: Artificial Sequence
<220> FEATURE:
<223> OTHER INFORMATION: Aptamer

<400> SEQUENCE: 3
gggaggacga ugcggauccu cgucccguca cggcagaacc acgucaggcc uucaacagac    60
gacucgcuga ggauccgaga                                                80
```